(12) United States Patent
O'Connell et al.

(10) Patent No.: US 8,795,241 B2
(45) Date of Patent: Aug. 5, 2014

(54) DEPLOYMENT CATHETER

(75) Inventors: Desmond O'Connell, Lake Forest Park, WA (US); Erik Liljegren, Kirkland, WA (US); David H. Dillard, Grapeview, WA (US); Hugo X. Gonzalez, Woodinville, WA (US)

(73) Assignee: Spiration, Inc., Redmond, WA (US)

( * ) Notice: Subject to any disclaimer, the term of this patent is extended or adjusted under 35 U.S.C. 154(b) by 67 days.

(21) Appl. No.: 13/107,564

(22) Filed: May 13, 2011

(65) Prior Publication Data
US 2012/0289772 A1    Nov. 15, 2012

(51) Int. Cl.
*A61M 25/00*    (2006.01)

(52) U.S. Cl.
USPC ......................................................... 604/264

(58) Field of Classification Search
CPC ............ A61B 1/018; A61B 17/29; A61B 1/12
USPC ......... 128/200.24; 604/174–175, 264, 9, 514, 604/218; 606/1.11, 1.24, 2.11, 153, 151, 606/108; 600/104, 435, 37, 30, 101
See application file for complete search history.

(56) References Cited

U.S. PATENT DOCUMENTS

| | | | |
|---|---|---|---|
| 2,115,298 | A | 4/1938 | Brown |
| 2,832,078 | A | 4/1958 | Williams |
| 2,981,254 | A | 4/1961 | Vanderbilt |
| 3,320,972 | A | 5/1967 | High et al. |
| 3,370,305 | A | 2/1968 | Goott et al. |
| 3,445,916 | A | 5/1969 | Schulte |
| 3,472,230 | A | 10/1969 | Forgarty |
| 3,540,431 | A | 11/1970 | Modin-Uddin |
| 3,617,060 | A | 11/1971 | Iezzi |
| 3,657,744 | A | 4/1972 | Ersek |
| 3,671,979 | A | 6/1972 | Moulopoulos |
| 3,683,913 | A | 8/1972 | Kurtz et al. |
| 3,757,783 | A | 9/1973 | Alley |
| 3,760,808 | A | 9/1973 | Bleuer |
| 3,788,327 | A | 1/1974 | Donowitz et al. |

(Continued)

FOREIGN PATENT DOCUMENTS

| | | |
|---|---|---|
| CA | 2308186 | 5/1999 |
| CN | 101868199 | 10/2010 |

(Continued)

OTHER PUBLICATIONS

U.S. Appl. No. 12/249,243, filed Oct. 10, 2008, and its ongoing prosecution history including without limitation Office Actions, Amendments, Remarks, and any other potentially relevant documents.

(Continued)

*Primary Examiner* — John P Leubecker
*Assistant Examiner* — Ronald D Colque
(74) *Attorney, Agent, or Firm* — Knobbe Martens Olson & Bear LLP

(57) ABSTRACT

A deployment catheter is described herein that preferably is configured to deliver a medical device such as a valve to a location in a patient such as a patient's airway. Preferably, such a deployment catheter is configured to be used in conjunction with a bronchoscope. In some embodiments, a locking lever is provided to reduce the likelihood of accidental deployment of the device, and which resets conveniently after use to as to permit multiple device deployments.

18 Claims, 30 Drawing Sheets

(56) References Cited

U.S. PATENT DOCUMENTS

| | | |
|---|---|---|
| 3,874,388 A | 4/1975 | King et al. |
| 3,889,657 A | 6/1975 | Baumgarten |
| 4,014,318 A | 3/1977 | Dockum et al. |
| 4,040,428 A | 8/1977 | Clifford |
| 4,056,854 A | 11/1977 | Boretos et al. |
| 4,075,959 A | 2/1978 | Zocher |
| 4,084,268 A | 4/1978 | Ionescu et al. |
| 4,086,665 A | 5/1978 | Poirlier |
| 4,205,282 A | 5/1980 | Gipprich |
| 4,212,463 A | 7/1980 | Repinski et al. |
| 4,218,782 A | 8/1980 | Rygg |
| 4,222,126 A | 9/1980 | Boretos et al. |
| 4,250,873 A | 2/1981 | Bonnet |
| 4,267,839 A | 5/1981 | Laufe et al. |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,393,879 A | 7/1983 | Milgrom |
| 4,402,445 A | 9/1983 | Green |
| 4,403,616 A | 9/1983 | King |
| 4,456,016 A | 6/1984 | Nowacki et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,583,541 A | 4/1986 | Barry |
| 4,592,741 A | 6/1986 | Vincent |
| 4,601,465 A | 7/1986 | Roy |
| 4,610,256 A | 9/1986 | Wallace |
| 4,619,246 A | 10/1986 | Molgaard-Nielsen et al. |
| 4,654,027 A | 3/1987 | Dragan et al. |
| 4,654,029 A | 3/1987 | D'Antonio |
| 4,681,110 A | 7/1987 | Wiktor |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,799,311 A | 1/1989 | Cosmetto et al. |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,552 A | 8/1989 | Chaux |
| 4,852,568 A | 8/1989 | Kensey |
| 4,870,975 A | 10/1989 | Cronk et al. |
| 4,877,025 A | 10/1989 | Hanson |
| 4,881,939 A | 11/1989 | Newman |
| 4,888,015 A | 12/1989 | Domino |
| 4,896,668 A | 1/1990 | Popoff et al. |
| 4,908,028 A | 3/1990 | Colon et al. |
| 4,920,978 A | 5/1990 | Colvin |
| 4,934,999 A | 6/1990 | Bader |
| 4,936,823 A | 6/1990 | Colvin et al. |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 4,995,872 A | 2/1991 | Ferrara |
| 5,019,086 A | 5/1991 | Neward |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,111,823 A | 5/1992 | Komberg et al. |
| 5,116,360 A | 5/1992 | Pinchuk et al. |
| 5,116,564 A | 5/1992 | Jansen et al. |
| 5,123,919 A | 6/1992 | Sauter et al. |
| 5,127,412 A | 7/1992 | Csometto et al. |
| 5,135,488 A | 8/1992 | Foote et al. |
| 5,135,531 A | 8/1992 | Shiber |
| 5,147,369 A | 9/1992 | Wagner |
| 5,151,105 A | 9/1992 | Kwan-Gett |
| 5,158,548 A | 10/1992 | Lau et al. |
| 5,161,524 A | 11/1992 | Evans |
| 5,171,299 A | 12/1992 | Heitzmann et al. |
| 5,186,711 A | 2/1993 | Epstein |
| 5,197,485 A | 3/1993 | Grooters |
| 5,197,963 A | 3/1993 | Parins |
| 5,197,980 A | 3/1993 | Gorshkov et al. |
| 5,207,702 A | 5/1993 | Pearl |
| 5,226,429 A | 7/1993 | Kuzmak |
| 5,255,687 A | 10/1993 | McKenna |
| 5,275,169 A | 1/1994 | Afromowitz et al. |
| 5,281,229 A | 1/1994 | Neward |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels |
| 5,350,388 A | 9/1994 | Epstein |
| 5,352,240 A | 10/1994 | Ross |
| 5,353,470 A | 10/1994 | Bartlett |
| 5,356,412 A | 10/1994 | Golds et al. |
| 5,358,518 A | 10/1994 | Camilli |
| 5,366,475 A | 11/1994 | Voss et al. |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolby |
| 5,391,205 A | 2/1995 | Knight |
| 5,392,775 A | 2/1995 | Adkins, Jr. et al. |
| 5,398,844 A | 3/1995 | Zaslavsky |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Andersen et al. |
| 5,413,599 A | 5/1995 | Imachi et al. |
| 5,415,658 A | 5/1995 | Kipela et al. |
| 5,415,660 A | 5/1995 | Campbell et al. |
| 5,417,226 A | 5/1995 | Juma |
| 5,421,325 A | 6/1995 | Cinberg et al. |
| 5,423,830 A | 6/1995 | Schneebaum et al. |
| 5,445,626 A | 8/1995 | Gigante |
| 5,453,090 A | 9/1995 | Martenez et al. |
| 5,456,689 A | 10/1995 | Kresch et al. |
| 5,459,544 A | 10/1995 | Emura |
| 5,484,444 A | 1/1996 | Braunschweiler et al. |
| 5,486,154 A | 1/1996 | Kelleher |
| 5,490,860 A | 2/1996 | Middle et al. |
| 5,499,995 A | 3/1996 | Teirstein |
| 5,500,014 A | 3/1996 | Quijano et al. |
| RE35,225 E | 4/1996 | Herweck et al. |
| 5,503,638 A | 4/1996 | Cooper |
| 5,507,754 A | 4/1996 | Green et al. |
| 5,507,797 A | 4/1996 | Suzuki |
| 5,509,900 A | 4/1996 | Kirkman |
| 5,514,153 A | 5/1996 | Bonutti et al. |
| 5,549,626 A | 8/1996 | Miller et al. |
| 5,549,628 A | 8/1996 | Cooper et al. |
| 5,562,608 A | 10/1996 | Sekins et al. |
| 5,562,641 A | 10/1996 | Flomenblit et al. |
| 5,562,728 A | 10/1996 | Lazarus et al. |
| 5,575,293 A | 11/1996 | Miller et al. |
| 5,593,413 A | 1/1997 | Alexander |
| 5,603,698 A | 2/1997 | Roberts et al. |
| 5,607,469 A | 3/1997 | Frey |
| 5,645,565 A | 7/1997 | Rudd et al. |
| 5,647,857 A | 7/1997 | Andersen et al. |
| 5,660,175 A | 8/1997 | Dayal |
| 5,662,622 A | 9/1997 | Gore et al. |
| 5,662,713 A | 9/1997 | Andersen et al. |
| 5,669,933 A | 9/1997 | Simon et al. |
| 5,676,671 A | 10/1997 | Inoue |

(56) References Cited

U.S. PATENT DOCUMENTS

| | | |
|---|---|---|
| 5,683,451 A | 11/1997 | Lenker et al. |
| 5,690,644 A | 11/1997 | Yurek et al. |
| 5,693,069 A | 12/1997 | Shallman |
| 5,693,089 A | 12/1997 | Inoue |
| 5,697,968 A | 12/1997 | Rogers et al. |
| 5,702,343 A | 12/1997 | Alferness |
| 5,702,409 A | 12/1997 | Rayburn et al. |
| 5,725,519 A | 3/1998 | Penner et al. |
| 5,741,271 A | 4/1998 | Nakao et al. |
| 5,752,522 A | 5/1998 | Murphy |
| 5,752,965 A | 5/1998 | Francis et al. |
| 5,755,770 A | 5/1998 | Ravenscroft |
| 5,763,979 A | 6/1998 | Mukherjee et al. |
| 5,766,134 A | 6/1998 | Lisak et al. |
| 5,769,892 A | 6/1998 | Kingwell |
| 5,772,583 A | 6/1998 | Wright et al. |
| 5,779,649 A | 7/1998 | Nicholas |
| 5,782,896 A | 7/1998 | Chen et al. |
| 5,797,907 A | 8/1998 | Clement |
| 5,797,920 A | 8/1998 | Kim |
| 5,797,960 A | 8/1998 | Stevens et al. |
| 5,800,339 A | 9/1998 | Salama |
| 5,803,078 A | 9/1998 | Brauner |
| 5,810,806 A | 9/1998 | Ritchart et al. |
| 5,810,809 A | 9/1998 | Rydell |
| 5,810,837 A | 9/1998 | Hofmann et al. |
| 5,810,855 A | 9/1998 | Rayburn et al. |
| 5,817,101 A | 10/1998 | Fiedler |
| 2,479,805 A | 11/1998 | Sabaratnam |
| 5,830,217 A | 11/1998 | Ryan |
| 5,833,694 A | 11/1998 | Poncet |
| 5,840,081 A | 11/1998 | Andersen et al. |
| 5,851,232 A | 12/1998 | Lois |
| 5,855,587 A | 1/1999 | Hyon |
| 5,855,597 A | 1/1999 | Jayaraman |
| 5,855,601 A | 1/1999 | Bessler et al. |
| 5,865,724 A | 2/1999 | Palmer et al. |
| 5,876,434 A | 3/1999 | Flomenblit et al. |
| 5,876,445 A | 3/1999 | Andersen et al. |
| 5,895,387 A | 4/1999 | Guerrero et al. |
| 5,902,312 A | 5/1999 | Frater et al. |
| 5,911,756 A | 6/1999 | Debry |
| 5,925,063 A | 7/1999 | Khosravi |
| 5,944,738 A | 8/1999 | Amplatz et al. |
| 5,947,997 A | 9/1999 | Pavcnik et al. |
| 5,954,636 A | 9/1999 | Schwartz et al. |
| 5,954,766 A | 9/1999 | Zadno-Azizi et al. |
| 5,957,949 A | 9/1999 | Leonhardt et al. |
| 5,957,978 A | 9/1999 | Blom |
| 5,972,009 A | 10/1999 | Fortier et al. |
| 5,976,158 A | 11/1999 | Adams et al. |
| 5,976,174 A | 11/1999 | Ruiz |
| 5,980,545 A | 11/1999 | Pacala et al. |
| 5,984,965 A | 11/1999 | Knapp et al. |
| 5,989,234 A | 11/1999 | Valerio et al. |
| 6,003,517 A | 12/1999 | Sheffield et al. |
| 6,007,575 A | 12/1999 | Samuels |
| 6,009,614 A | 1/2000 | Morales |
| 6,010,511 A | 1/2000 | Murphy |
| 6,010,525 A | 1/2000 | Bonutti et al. |
| 6,020,380 A | 2/2000 | Killian |
| 6,024,759 A | 2/2000 | Nuss et al. |
| 6,027,525 A | 2/2000 | Suh et al. |
| 6,045,560 A | 4/2000 | McKean et al. |
| 6,051,022 A | 4/2000 | Cai et al. |
| 6,053,877 A | 4/2000 | Banik et al. |
| 6,062,575 A | 5/2000 | Mickel et al. |
| 6,068,635 A | 5/2000 | Gianotti |
| 6,068,638 A | 5/2000 | Makower |
| 6,077,214 A | 6/2000 | Schweich et al. |
| 6,077,291 A | 6/2000 | Das |
| 6,079,413 A | 6/2000 | Baran |
| 6,083,141 A | 7/2000 | Hougen |
| 6,083,255 A | 7/2000 | Laufer et al. |
| 6,086,543 A | 7/2000 | Anderson et al. |
| 6,090,035 A | 7/2000 | Campbell et al. |
| 6,090,041 A | 7/2000 | Clark |
| 6,096,027 A | 8/2000 | Layne |
| 6,099,551 A | 8/2000 | Gabbay |
| 6,102,885 A | 8/2000 | Bass |
| 6,102,926 A | 8/2000 | Tartaglia et al. |
| 6,123,663 A | 9/2000 | Rebuffat |
| 6,132,458 A | 10/2000 | Staehle et al. |
| 6,135,729 A | 10/2000 | Aber |
| 6,135,991 A | 10/2000 | Muni et al. |
| 6,141,855 A | 11/2000 | Morales |
| 6,142,957 A | 11/2000 | Diamond et al. |
| 6,146,357 A | 11/2000 | Addis |
| 6,146,384 A | 11/2000 | Lee et al. |
| 6,146,388 A | 11/2000 | McDonald |
| 6,149,664 A | 11/2000 | Kurz |
| 6,162,245 A | 12/2000 | Jayaraman |
| 6,165,179 A | 12/2000 | Cathcart et al. |
| 6,168,614 B1 | 1/2001 | Andersen et al. |
| 6,168,617 B1 | 1/2001 | Blaeser et al. |
| 6,174,307 B1 | 1/2001 | Daniel et al. |
| 6,174,323 B1 | 1/2001 | Biggs |
| 6,183,520 B1 | 2/2001 | Pintauro et al. |
| 6,193,748 B1 | 2/2001 | Thompson et al. |
| 6,200,333 B1 | 3/2001 | Laufer |
| 6,203,551 B1 | 3/2001 | Wu |
| 6,206,918 B1 | 3/2001 | Campbell et al. |
| 6,210,338 B1 | 4/2001 | Afremov et al. |
| 6,213,957 B1 | 4/2001 | Milliman et al. |
| 6,231,587 B1 | 5/2001 | Makower |
| 6,231,589 B1 | 5/2001 | Wessman et al. |
| 6,234,996 B1 | 5/2001 | Bagaoisan et al. |
| 6,238,334 B1 | 5/2001 | Easterbrook, III et al. |
| 6,240,615 B1 | 6/2001 | Kimes et al. |
| 6,241,654 B1 | 6/2001 | Alferness |
| 6,241,678 B1 | 6/2001 | Afremov et al. |
| 6,241,758 B1 | 6/2001 | Cox |
| 6,242,472 B1 | 6/2001 | Sekins et al. |
| 6,245,102 B1 | 6/2001 | Jayaraman |
| 6,258,100 B1 | 7/2001 | Alferness et al. |
| 6,264,700 B1 | 7/2001 | Kilcoyne et al. |
| 6,267,775 B1 | 7/2001 | Clerc et al. |
| 6,270,527 B1 | 8/2001 | Campbell et al. |
| 6,277,083 B1 | 8/2001 | Eggers et al. |
| 6,280,398 B1 | 8/2001 | Ritchart et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,296,639 B1 | 10/2001 | Truckai et al. |
| 6,299,604 B1 | 10/2001 | Ragheb et al. |
| 6,302,893 B1 | 10/2001 | Limon et al. |
| 6,312,407 B1 | 11/2001 | Zadno-Azizi et al. |
| 6,322,522 B1 | 11/2001 | Zimmon |
| 6,325,777 B1 | 12/2001 | Zadno-Azizi et al. |
| 6,325,778 B1 | 12/2001 | Zadno-Azizi et al. |
| 6,327,505 B1 | 12/2001 | Medhkour et al. |
| 6,327,772 B1 | 12/2001 | Zadno-Azizi et al. |
| 6,328,689 B1 | 12/2001 | Gonzalez et al. |
| 6,338,728 B1 | 1/2002 | Valerio et al. |
| 6,350,278 B1 | 2/2002 | Lenker et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,425,916 B1 | 7/2002 | Garrison et al. |
| 6,428,561 B1 | 8/2002 | Johansson-Ruden et al. |
| 6,439,233 B1 | 8/2002 | Geertsema |
| 6,440,164 B1 | 8/2002 | DiMatteo et al. |
| 6,447,530 B1 | 9/2002 | Ostrovsky et al. |
| 6,454,727 B1 | 9/2002 | Burbank et al. |
| 6,454,754 B1 | 9/2002 | Frank |
| 6,458,076 B1 | 10/2002 | Pruitt |
| 6,458,153 B1 | 10/2002 | Bailey et al. |
| 6,471,718 B1 | 10/2002 | Staehle et al. |
| 6,471,979 B2 | 10/2002 | New et al. |
| 6,485,407 B2 | 11/2002 | Alferness et al. |
| 6,485,436 B1 | 11/2002 | Truckai et al. |
| 6,488,673 B1 | 12/2002 | Laufer |
| 6,491,706 B1 | 12/2002 | Alferness et al. |

(56) References Cited

U.S. PATENT DOCUMENTS

| | | | |
|---|---|---|---|
| 6,493,589 B1 | 12/2002 | Medhkour et al. |
| 6,503,272 B2 | 1/2003 | Duerig et al. |
| 6,506,166 B1 | 1/2003 | Hendler et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,540,782 B1 | 4/2003 | Snyders |
| 6,544,192 B2 | 4/2003 | Starr et al. |
| 6,544,291 B2 | 4/2003 | Taylor |
| 6,551,255 B2 | 4/2003 | Van Bladel et al. |
| 6,558,429 B2 | 5/2003 | Taylor |
| 6,568,387 B2 | 5/2003 | Davenport et al. |
| 6,569,166 B2 | 5/2003 | Gonzalez |
| 6,585,639 B1 | 7/2003 | Kotmel et al. |
| 6,589,240 B2 | 7/2003 | Hinchliffe |
| 6,589,256 B2 | 7/2003 | Forber |
| 6,592,594 B2 | 7/2003 | Rimbaugh et al. |
| 6,599,311 B1 | 7/2003 | Biggs et al. |
| 6,600,307 B2 | 7/2003 | Turski |
| 6,610,043 B1 | 8/2003 | Ingenito |
| 6,620,095 B2 | 9/2003 | Taheri |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,285 B2 | 10/2003 | Gabbay |
| 6,648,897 B2 | 11/2003 | Hamilton |
| 6,669,724 B2 | 12/2003 | Park et al. |
| 6,673,070 B2 | 1/2004 | Edwards et al. |
| 6,679,264 B1 | 1/2004 | Deem et al. |
| 6,682,250 B2 | 1/2004 | Banks |
| 6,682,520 B2 | 1/2004 | Ingenito |
| 6,694,979 B2 | 2/2004 | Deem et al. |
| 6,709,401 B2 | 3/2004 | Perkins et al. |
| 6,712,812 B2 | 3/2004 | Roschak et al. |
| 6,716,208 B2 | 4/2004 | Humes |
| 6,722,360 B2 | 4/2004 | Doshi |
| 6,743,259 B2 | 6/2004 | Ginn |
| 6,746,686 B2 | 6/2004 | Hughes et al. |
| 6,749,606 B2 | 6/2004 | Keast et al. |
| 6,749,658 B1 | 6/2004 | DeVore et al. |
| 6,840,952 B2 | 1/2005 | Saker et al. |
| 6,849,049 B2 | 2/2005 | Starr et al. |
| 6,849,084 B2 | 2/2005 | Rabkin et al. |
| 6,852,108 B2 | 2/2005 | Barry et al. |
| 6,860,847 B2 | 3/2005 | Alferness et al. |
| 6,887,256 B2 | 5/2005 | Gilson |
| 6,904,909 B2 | 6/2005 | Andreas et al. |
| 6,911,028 B2 | 6/2005 | Shadduck |
| 6,929,637 B2 | 8/2005 | Gonzalez et al. |
| 6,941,950 B2 | 9/2005 | Wilson et al. |
| 6,951,571 B1 | 10/2005 | Srivastava |
| 6,955,675 B2 | 10/2005 | Jain |
| 6,958,059 B2 | 10/2005 | Zadno-Azizi |
| 6,958,076 B2 | 10/2005 | Acosta et al. |
| 6,989,027 B2 | 1/2006 | Allen et al. |
| 6,997,951 B2 | 2/2006 | Solem et al. |
| 7,011,094 B2 | 3/2006 | Rapacki et al. |
| 7,077,851 B2 | 7/2006 | Lutze et al. |
| 7,086,398 B2 | 8/2006 | Tanaka |
| 7,100,616 B2 | 9/2006 | Springmeyer |
| 7,141,046 B2 | 11/2006 | Perkins et al. |
| 7,169,140 B1 | 1/2007 | Kume |
| 7,175,644 B2 | 2/2007 | Cooper et al. |
| 7,207,946 B2 | 4/2007 | Sirokman |
| 7,232,414 B2 | 6/2007 | Gonzalez |
| 7,252,086 B2 | 8/2007 | Tanaka |
| 7,273,469 B1 | 9/2007 | Chan et al. |
| 7,278,430 B2 | 10/2007 | Kumar |
| 7,344,553 B2 | 3/2008 | Opolski et al. |
| 7,357,795 B2 | 4/2008 | Kaji et al. |
| 7,412,977 B2 | 8/2008 | Fields et al. |
| 7,422,584 B2 | 9/2008 | Loomas et al. |
| 7,434,578 B2 | 10/2008 | Dillard et al. |
| 7,476,203 B2 | 1/2009 | DeVore et al. |
| 7,530,995 B2 | 5/2009 | Quijano et al. |
| 7,533,671 B2 | 5/2009 | Gonzalez et al. |
| 7,637,934 B2 | 12/2009 | Mangiardi et al. |
| 7,691,151 B2 | 4/2010 | Kutsko |
| 7,757,692 B2 | 7/2010 | Alferness et al. |
| 7,798,974 B2 | 9/2010 | Sirokman |
| 7,842,010 B2 | 11/2010 | Dillard et al. |
| 7,842,061 B2 | 11/2010 | Dillard et al. |
| 7,854,228 B2 | 12/2010 | Wilson et al. |
| 7,875,048 B2 | 1/2011 | Dillard et al. |
| 7,887,585 B2 | 2/2011 | Gonzalez et al. |
| 7,896,887 B2 | 3/2011 | Rimbaugh et al. |
| 7,913,698 B2 | 3/2011 | Barry et al. |
| 7,942,931 B2 | 5/2011 | Gonzalez et al. |
| 8,136,230 B2 * | 3/2012 | Adams et al. ............... 29/718 |
| 2001/0010017 A1 | 7/2001 | Letac et al. |
| 2002/0029004 A1 | 3/2002 | Starr et al. |
| 2002/0072730 A1 | 6/2002 | McGill et al. |
| 2002/0077564 A1 | 6/2002 | Campbell et al. |
| 2002/0077593 A1 | 6/2002 | Perkins et al. |
| 2002/0077696 A1 | 6/2002 | Zadno-Azizi et al. |
| 2002/0095209 A1 | 7/2002 | Zadno-Azizi et al. |
| 2002/0147462 A1 | 10/2002 | Mair et al. |
| 2003/0018327 A1 | 1/2003 | Truckai et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0083730 A1 | 5/2003 | Stinson |
| 2003/0125763 A1 | 7/2003 | McInnes |
| 2003/0127090 A1 | 7/2003 | Gifford et al. |
| 2003/0154988 A1 | 8/2003 | DeVore et al. |
| 2003/0181890 A1 | 9/2003 | Schulze et al. |
| 2003/0181922 A1 | 9/2003 | Eaton et al. |
| 2003/0183235 A1 | 10/2003 | Rimbaugh et al. |
| 2003/0195385 A1 | 10/2003 | DeVore |
| 2003/6632243 | 10/2003 | Zadno-Azizi et al. |
| 2003/0212337 A1 | 11/2003 | Sirokman |
| 2003/0212412 A1 | 11/2003 | Dillard et al. |
| 2003/0216769 A1 | 11/2003 | Dillard et al. |
| 2003/0225445 A1 | 12/2003 | Derus et al. |
| 2004/0010209 A1 | 1/2004 | Sirokman |
| 2004/0024356 A1 | 2/2004 | Tanaka |
| 2004/0039250 A1 | 2/2004 | Tholfsen et al. |
| 2004/0040555 A1 | 3/2004 | Tanaka |
| 2004/0059263 A1 | 3/2004 | DeVore |
| 2004/0127912 A1 * | 7/2004 | Rabkin et al. ............... 606/108 |
| 2004/0143282 A1 | 7/2004 | Dillard et al. |
| 2004/0194780 A1 | 10/2004 | Doshi |
| 2004/0206349 A1 | 10/2004 | Alferness et al. |
| 2004/0211412 A1 | 10/2004 | Alferness et al. |
| 2004/0211434 A1 | 10/2004 | Loomas et al. |
| 2004/0243140 A1 | 12/2004 | Alferness et al. |
| 2005/0033310 A1 | 2/2005 | Alferness et al. |
| 2005/0080434 A1 | 4/2005 | Chung et al. |
| 2005/0096721 A1 | 5/2005 | Mangin et al. |
| 2005/0137611 A1 | 6/2005 | Escudero et al. |
| 2005/0145253 A1 | 7/2005 | Wilson et al. |
| 2005/0149159 A1 * | 7/2005 | Andreas et al. ............... 623/1.11 |
| 2005/0222580 A1 | 10/2005 | Gifford, III et al. |
| 2005/0245894 A1 | 11/2005 | Zadno-Azizi |
| 2005/0267323 A1 | 12/2005 | Dorros et al. |
| 2006/0032497 A1 | 2/2006 | Doshi |
| 2006/0064123 A1 | 3/2006 | Bonnette et al. |
| 2006/0074382 A1 | 4/2006 | Gonzalez et al. |
| 2006/0100687 A1 | 5/2006 | Fahey et al. |
| 2006/0200076 A1 | 9/2006 | Gonzalez et al. |
| 2006/0206147 A1 | 9/2006 | DeVore et al. |
| 2006/0235432 A1 | 10/2006 | DeVore |
| 2006/0235467 A1 | 10/2006 | DeVore |
| 2006/0249164 A1 | 11/2006 | Springmeyer |
| 2006/0270940 A1 | 11/2006 | Tsukashima et al. |
| 2007/0209204 A1 | 9/2007 | Chase et al. |
| 2007/0221230 A1 | 9/2007 | Thompson et al. |
| 2007/0225747 A1 | 9/2007 | Perkins et al. |
| 2008/0015627 A1 | 1/2008 | DeVore |
| 2008/0119866 A1 | 5/2008 | Alferness |
| 2008/0132989 A1 | 6/2008 | Snow et al. |
| 2008/0149446 A1 | 6/2008 | Schuurman |
| 2009/0099530 A1 | 4/2009 | Adams et al. |

(56) References Cited

U.S. PATENT DOCUMENTS

| | | | |
|---|---|---|---|
| 2009/0205667 A1* | 8/2009 | Alferness et al. | 128/207.15 |
| 2009/0292262 A1 | 11/2009 | Adams et al. | |
| 2010/0082089 A1 | 4/2010 | Quadri et al. | |
| 2010/0174363 A1* | 7/2010 | Castro | 623/2.11 |
| 2010/0256714 A1 | 10/2010 | Springmeyer | |
| 2010/0262071 A1 | 10/2010 | Kutsko et al. | |
| 2010/0305715 A1* | 12/2010 | Mathis et al. | 623/23.65 |
| 2011/0054632 A1 | 3/2011 | Alferness | |
| 2011/0071490 A1* | 3/2011 | Kassab et al. | 604/500 |
| 2011/0079221 A1 | 4/2011 | Dillard | |

FOREIGN PATENT DOCUMENTS

| | | |
|---|---|---|
| CN | 102058443 | 5/2011 |
| DE | 100 04 979 | 8/2000 |
| EP | 0 665 029 | 8/1995 |
| EP | 0 743 071 | 11/1996 |
| EP | 1 078 601 | 2/2001 |
| EP | 1 151 729 | 11/2001 |
| EP | 1 157 663 | 11/2001 |
| EP | 1 206 276 | 5/2002 |
| EP | 1 198 269 | 10/2009 |
| EP | 2 353 557 | 8/2011 |
| FR | 2 773 702 | 7/1999 |
| GB | 2 082 071 | 3/1982 |
| GB | 2 324 729 | 11/1998 |
| GB | 2 348 138 | 9/2000 |
| JP | 58-163332 | 9/1983 |
| JP | 60-10740 | 1/1994 |
| JP | H08-19544 | 1/1996 |
| JP | 10-503411 | 3/1998 |
| JP | 2003-503162 | 1/2003 |
| JP | 2004-535887 | 12/2004 |
| JP | 2005-527297 | 9/2005 |
| JP | 3742010 | 11/2005 |
| JP | 2008-194250 | 8/2008 |
| JP | 4387803 B2 | 10/2009 |
| JP | 2011-500171 | 1/2011 |
| RU | 2140211 | 10/1999 |
| SU | 852321 | 8/1981 |
| SU | 1371700 | 2/1988 |
| SU | 1593651 | 9/1990 |
| WO | WO 88/09683 | 12/1988 |
| WO | WO 90/03152 | 4/1990 |
| WO | WO 94/26175 | 11/1994 |
| WO | WO 95/32018 | 11/1995 |
| WO | WO 96/04875 | 2/1996 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/08441 | 3/1998 |
| WO | WO 98/19633 | 5/1998 |
| WO | WO 98/39047 | 9/1998 |
| WO | WO 98/44854 | 10/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/12011 | 3/2000 |
| WO | WO 00/18329 | 4/2000 |
| WO | WO 00/27292 A | 5/2000 |
| WO | WO 00/42950 | 7/2000 |
| WO | WO 00/51500 A | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/15604 | 3/2001 |
| WO | WO 01/28433 | 4/2001 |
| WO | WO 01/30266 A | 5/2001 |
| WO | WO 01/37897 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO 01/66190 | 9/2001 |
| WO | WO 01/70114 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22053 | 3/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069808 | 9/2002 |
| WO | WO 02/069823 | 9/2002 |
| WO | WO 02/087447 | 11/2002 |
| WO | WO 02/094087 | 11/2002 |
| WO | WO 03/022124 | 3/2003 |
| WO | WO 03/030975 | 4/2003 |
| WO | WO 03/003946 | 5/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/079944 | 10/2003 |
| WO | WO 03/088820 | 10/2003 |
| WO | WO 03/094996 | 11/2003 |
| WO | WO 03/099164 | 12/2003 |
| WO | WO 2004/010845 | 5/2004 |
| WO | WO 2004/080347 | 9/2004 |
| WO | WO 2005/013835 | 2/2005 |
| WO | WO 2006/124822 | 11/2006 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |

OTHER PUBLICATIONS

U.S. Appl. No. 12/422,179, filed Apr. 10, 2009, and its ongoing prosecution history including without limitation Office Actions, Amendments, Remarks, and any other potentially relevant documents.

April et al. "Correction of Funnel-Chest According to Senning-Johnson", Schweiz. Rundchau. Med. (PRAXIS) 79, Nr. 12 (1980) pp. 356-360.

Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.

Chest Drains, from webmaster@surgical-tutor.org.uk; from Website on Mar. 21, 2002; pp. 1-3.

(56) References Cited

OTHER PUBLICATIONS

Dillard et al.,"Evaluation of a Nvel Intra-bronchial Valve Device to Produce Lung Volume Reduction," Poster show at conference in Jun. 2002.
EDO Certamics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
EWS Endobronchial Watanabe Spigots, Novatech, edited Apr. 17, 2002.
Exploring Chest Drain Options; from webmaster google.com; RNWeb: Continuing Education; from website on Mar. 21, 2002; pp. 1-6.
Harris et al., "The Experimental Production in Dogs of Emphysema with Associated Asthatic Syndrome by Means of an Interatracheal Ball Valve," J Exp Med 30: 1919; 75-88.
Horiuchi et al: Three Cases of Intractable Pneumothorax Treated Sucessfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
Isakov et al. "A New Method of Surgical Treatment of Funnel Chest with Help of Permanent Magnets", Chir. Pediatr., 1980, 21, pp. 361-362.
J&J Gateway LLC Web Page: Steps in the MAMMOTOME Surgical Procedure; Surgical Technique, Dec. 28, 2001; p. 1-3.
Jones et al: Closure of a Benign Broncho-Oesophageal Fistula by Endoscopic Injection of Bovine Collagen, Cyanocrylate Glue and Gelfoam; 1996, pp. 53-55 Aust. N.Z. J.. Surg.
Lewis et al, "Pulmonary Interstitial Emphysema: Selective Bronchial Occlusion with a Swan-Ganz Catheter." Archives of Disease in Childhood, 63:1988, 313-315.
Marco: Bubble Detector, from webmaster@marco.de, from Website on Mar. 21, 2002; pp. 1-3.
Matthew et al. "Selective Bronchial Obstruction for Treatment of Bullous Interstitial Emphysema," J. of Ped. 96:1980, 475-477.
Oasis Dry Suction Chest Drains; Instructions for Use; Atrium Medical Corporation, Hudson New Hampshire, on Mar. 27, 2002, pp. 1-4.
Ochsner et al. "Chone-Chondrosternon", Journal of Thoracic Surgery, vol. 8, No. 5, Jun. 1939, pp. 469-511.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.
Puhakka et al., "Acute Bronchial Obstruction: An Experimental Rabbit Model Study." Int. J. of Pediatric Otorhinolaryngology. 18:1989, 107-118.
Shamberger, "Congenital Chest Wall Deformities" Current Problems in Surgery vol. XXXIII, No. 6, Jun. 1996, pp. 470-543.
SIII Control and Display Modules; from webmaster@stoeckert.de; from website on Mar. 21, 2002, pp. 1-5.
Snider et al., "The Definition of Emphysema: Report of the National Heart Lung and Blood Institute, Division of Lung Diseases Workshop", Am. Ev. Respir. Dis., 132:182-185, 1985.
Tube Thorascostomy; from webmaster@merck.com/pubs/mmanual; from Website Mar. 21, 2003, pp. 1,2.
Understanding Chest Drainage; from webmaster@nursingceu.com; from website on Mar. 21, 2002; pp. 1-15.
Watanabe et al: Bronchial Embolization Using Dental Impression Material in a Case of Pyelo-bronchial Fistula with *Candida* Fungemia; 1991. Journal of the Japan Society for Bronchology, pp. 607-610.
International Preliminary Report on Patentability for Application No. PCT/US2010/030131, dated Mar. 18, 2011.
International Report on Patentability dated Dec. 23, 2009 re PCT/US2008/079650.
International Search Report and Written Opinion for Application No. PCT/US2010/030131, dated Jun. 18, 2010.
International Search Report dated Jan. 30, 2009 re PCT/US2008/079650.
Japanese Notice of Reasons for Rejection, re JP Application No. 2012-504789, mailed Jan. 21, 2014.
International Search Report and Written Opinion for International Application No. PCT/US2011/36549, dates May 13, 2011; 14 pages.
Japanese Notice of Reasons for Rejection, re JP Application No. 2010-529122, dated Jul. 23, 2013.

\* cited by examiner

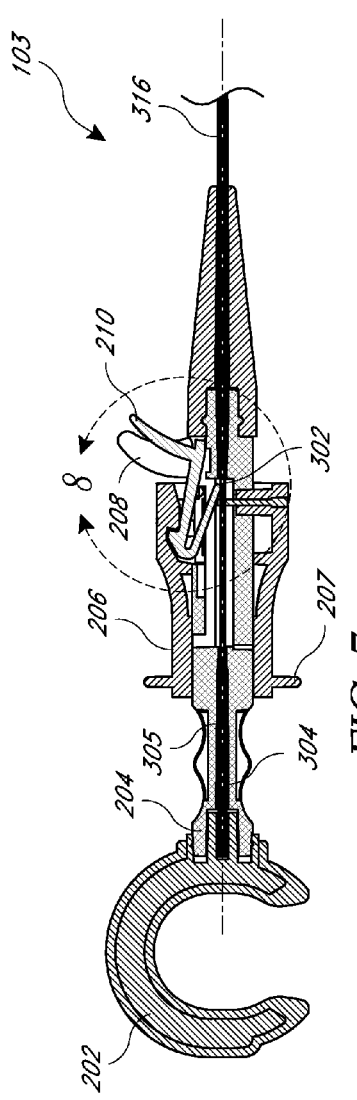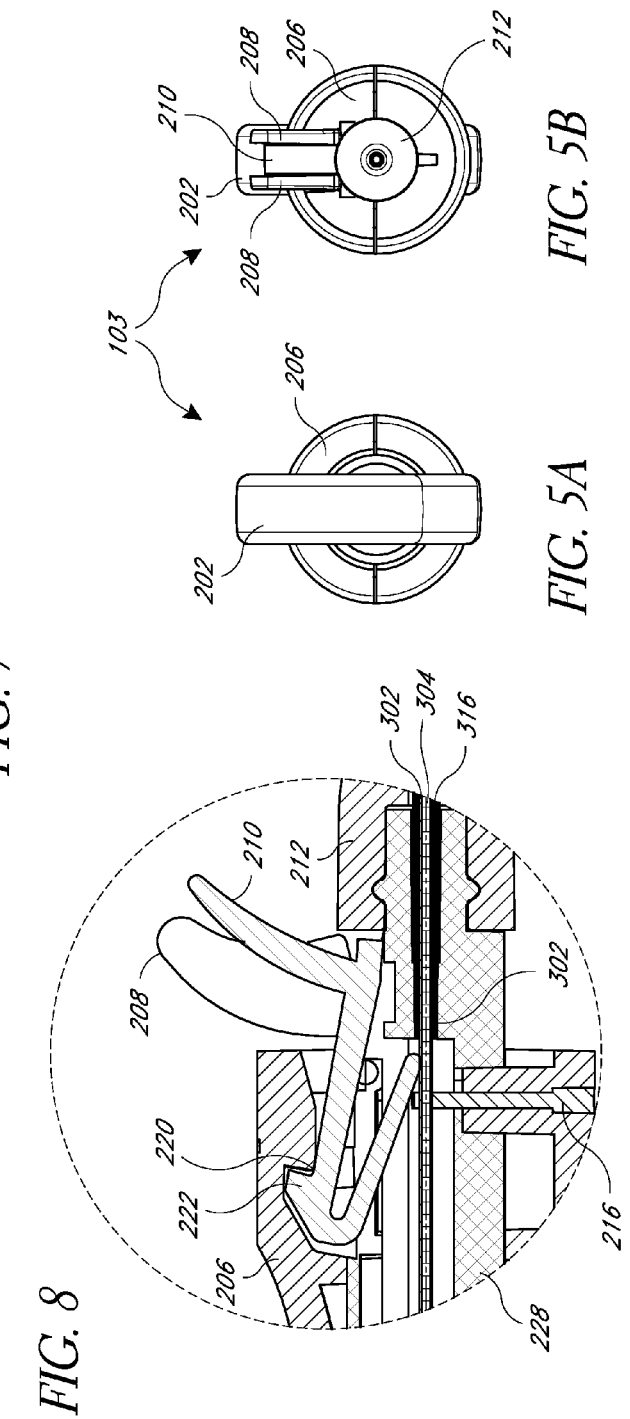

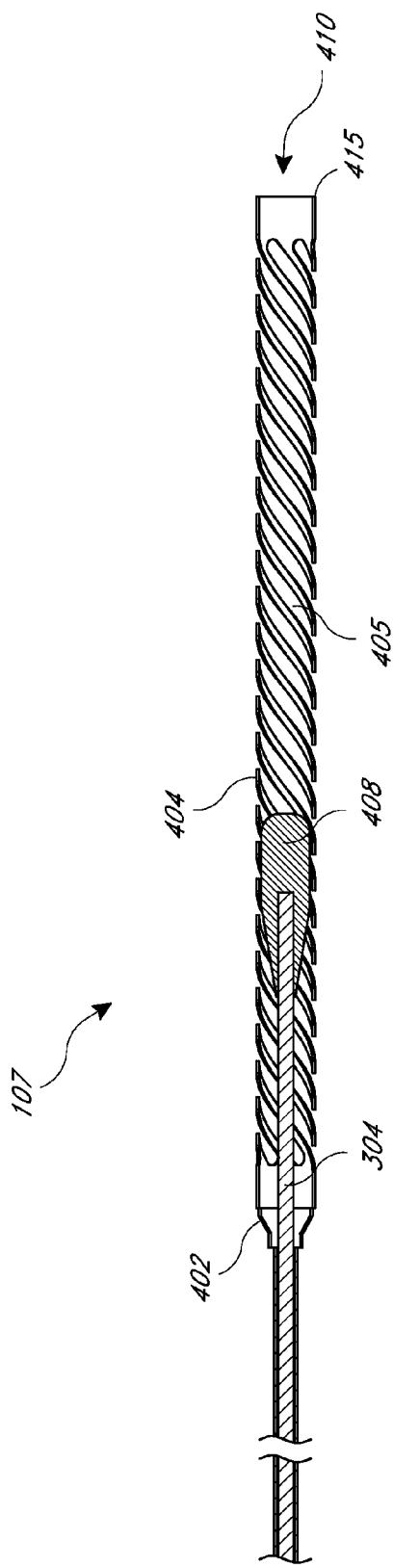
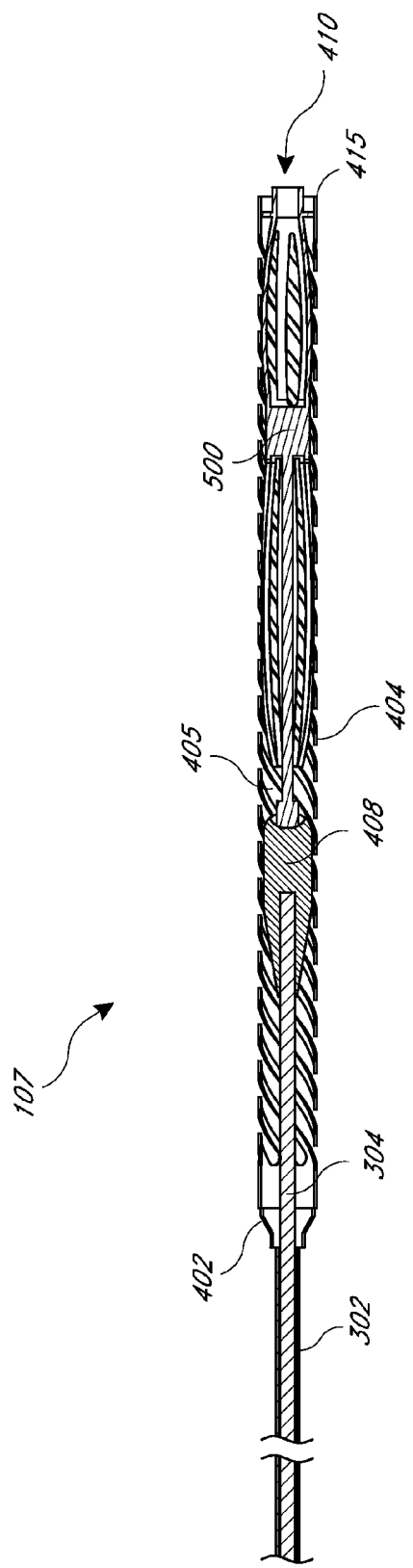
FIG. 12A
FIG. 12B

DEPLOYMENT CATHETER

BACKGROUND OF THE INVENTION

1. Field of the Invention

Embodiments of the invention generally relate to the field of medical devices, and in particular, to methods, systems, and devices for deploying and/or implanting a device such as a valve or other medical device into a body by using a catheter.

2. Description of the Related Art

The incidence, prevalence, and costs of pulmonary diseases such as COPD, chronic bronchitis, and emphysema have increased. New treatment methods include lung volume reduction treatment with minimally-invasive nonsurgical options. In these cases, valves may be implanted into the lungs of a patient to reduce lung size and/or treat air leaks. There is therefore a need for an apparatus and method to safely and consistently implant such valves or other medical devices into patient airways in order to treat lung conditions.

SUMMARY OF THE INVENTION

Embodiments of the invention generally relate to devices, systems, and methods for introducing a medical device such as a valve into a body via a catheter. A catheter is a tube that can be inserted into a body, or body cavity, duct or vessel. Catheters can be used to allow for drainage or injection of fluids to the body, or to provide access into the body by surgical instruments and/or implantable devices. In order to deliver an implantable device into a body, an implantable device may first be inserted into a catheter. To deliver the device to a suitable location, for example to an air passage in a lung, a bronchoscope or other device may be provided with a working channel into which the catheter may be introduced. Delivery and deployment of the device inserted in the catheter can then take place. In a preferred embodiment, a catheter loaded with a valve delivers the valve to a location in a lung airway.

A valve or other medical device, deployable or otherwise, can be introduced into a catheter or other deployment apparatus using the methods, systems, and devices described herein. The valve or other medical device can be implanted or positioned within a patient using a catheter or other deployment apparatus after the valve or other medical device has been loaded into the catheter or other deployment apparatus. Preferably, the valve or other medical device is loaded into a cavity or other space provided in the distal tip region of the catheter or other deployment apparatus. In some embodiments, the catheter or other deployment apparatus may be loaded into the working channel of a bronchoscope or other such apparatus and navigated to a suitable deployment location, for example a patient's airway.

Embodiments of the apparatus may have additional features, either alone or in combination, that may prove advantageous and useful in aiding deployment. For example, a lockout lever may be provided that reduces or eliminates the likelihood of accidental deployment of a valve or other device, and which may also reset after deployment so as to facilitate multiple device deployments. Additionally, a grip, which can in some embodiments be shaped as a C-handle, may be provided that can be clipped onto a bronchoscope to assist in deployment of a valve or other device, while also providing an ergonomic handle. Localization markers may also be provided on the apparatus, and in particular near its distal end, and which may aid an operator in aligning the implantable device with a chosen deployment site. The distal tip portion may also be constructed in a cage-like structure, and may also be provided with one or more fenestrations that may permit visualization of and confirmation that the valve or medical device has been correctly loaded into the distal tip. Of course, additional features and details will be discussed in greater detail herein.

In one embodiment, a deployment catheter for deploying a device into a lung is described, where the deployment catheter comprises:

a proximal end comprising a handle portion, the handle portion comprising a plunger, the plunger being surrounded by a movable handle, the movable handle configured to be slid axially in a direction along at least a portion of the length of the plunger, and wherein the plunger further comprises a locking lever capable of switching between locked and unlocked positions, the locking lever configured to prevent the movable handle from sliding in a proximal direction toward the plunger when in the locked position, but configured to permit the movable handle to slide in a proximal direction when in the unlocked position, and wherein the locking lever is further configured to reset to a locked position;

a catheter shaft portion, the catheter shaft portion comprising a catheter shaft and a stabilization wire inside the catheter shaft, wherein the catheter shaft is secured to the movable handle at the proximal end of the catheter shaft, and wherein the stabilization wire is secured to the plunger; and a distal tip portion configured to receive a medical device in a cavity, wherein the distal tip portion is secured to the distal end of the hollow catheter shaft, and which further comprises a pusher plunger received within the cavity, the pusher plunger connected to the distal end of the stabilization wire.

Some embodiments provide for the proximal plunger to comprise a C-shaped handle on its proximal end. In some embodiments, the locking lever comprises a locking tab configured to engage with a recess in the movable handle. The locking lever may also comprise a spring attached to the locking lever configured to reset the locking lever to a locked position after the medical device has been deployed from the deployment catheter.

In some embodiments, the catheter shaft portion comprises a high flexibility region at its distal end, which may comprise a jigsaw configuration, a serpentine configuration, or overlapping straight cuts.

Further embodiments provide for the distal tip portion to comprise a cage with at least one cavity configured to receive a medical device. The cage may have an arrangement of struts forming a spiral configuration, and may comprise one or more large fenestrations. In some embodiments, the one ore more large fenestrations are configured to permit visualization and confirmation that the medical device has been loaded into the cavity. The distal tip portion may also comprise at least one localization marker configured to indicate the approximate deployment location of the medical device. In some embodiments, the localization marker is yellow and flanked by two additional black bands. In some embodiments, the distal end of the catheter shaft portion further comprises at least one long localization marker.

In some embodiments, the handle portion further comprises a frustroconical strain relief surrounding a proximal region of the catheter shaft portion. Some embodiments may also comprise an outer sheath surrounding at least a proximal region of the catheter shaft portion. Preferred embodiments may be configured to be loaded within a bronchoscope.

A further embodiment provides for a method of deploying a medical device in a patient lung, where the method comprises:

loading the medical device into a cavity disposed in the distal tip portion of a deployment catheter;

introducing the deployment catheter into a bronchoscope;

inserting the bronchoscope into a lung airway;

navigating the bronchoscope to a portion of the lung airway to be treated;

aligning the portion of the lung airway to be treated with at least one localization marker disposed on the distal tip portion of the deployment catheter;

unlocking a locking lever on the deployment catheter; and deploying the medical device to the portion of the lung airway to be treated.

In some embodiments, the locking lever resets to a locked position after deployment of the device. In further embodiments, the deployment catheter comprises a C-shaped handle on its proximal end, and wherein the C-shaped handle is attached to a portion of the bronchoscope. In additional embodiments, the step of navigating the bronchoscope further comprises tracking the deployment catheter using radio imaging means.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIGS. 5A-B illustrate left and right views of an embodiment of the catheter.

FIG. 7 is a cross-section of an embodiment of the handle portion of the catheter.

FIG. 8 illustrates a close-up cross-section view of an embodiment of the catheter lockout mechanism.

FIGS. 12A-B respectively illustrate close-up cross-section views of an embodiment of the distal tip of the catheter without and with a valve loaded therein.

DETAILED DESCRIPTION OF THE PREFERRED EMBODIMENT

A catheter deployment system and its related components and parts now will be described with reference to the accompanying figures of one or more embodiments. The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

The terms "valve," "deployable medical device," and "medical device" and "device" as used herein are broad interchangeable terms and, unless otherwise indicated, the terms can include within their meanings, without limitation, stents, valves, lung reduction valves, balloons, probes, markers, including radioopaque markers and other forms of fiducial markers, anchors, or any other medical device, deployable or otherwise, that is configured to be loaded or introduced into a catheter or other deployment apparatus and subsequently delivered or deployed. Although some embodiments described herein refer to deploying a medical device into an airway, this disclosure is not so limited, and deployment could be made, for example but without limitation, into other vessels, passages, and body cavities in humans and animals. In certain embodiments, the valve and/or medical device is the type disclosed in U.S. Pat. Nos. 6,293,951 or 7,757,692, each of which is hereby incorporated in their entirety.

Figure 1:
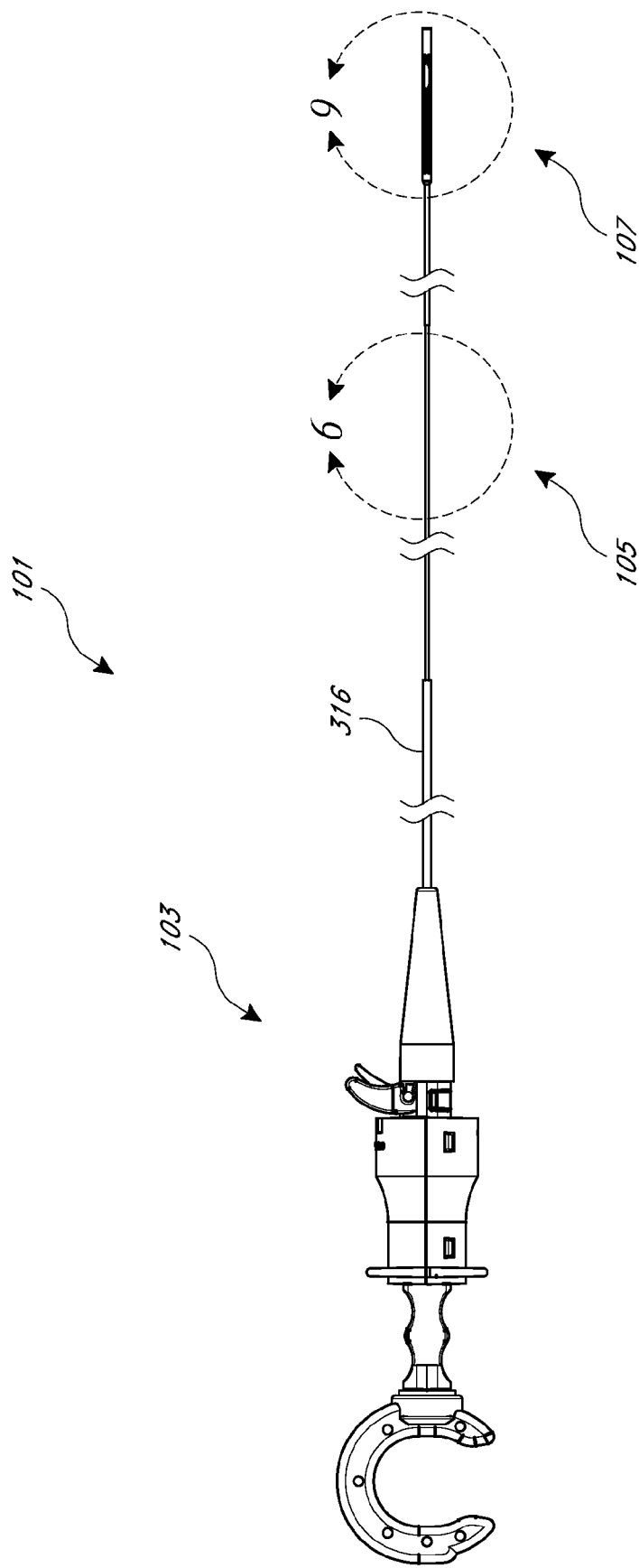
FIG. 1 illustrates a side view of an embodiment of a catheter.
Figure 2:
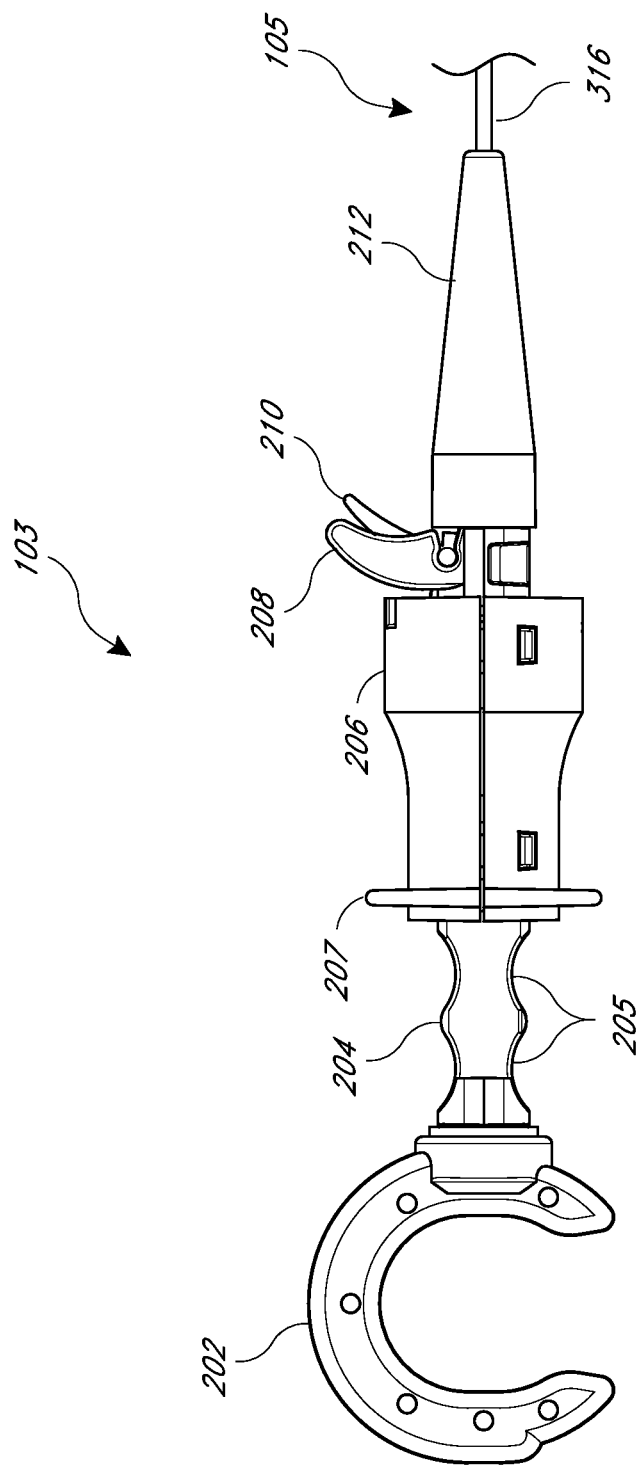
FIG. 2 illustrates a close-up side view of an embodiment of the handle portion of the catheter.
Figure 3:
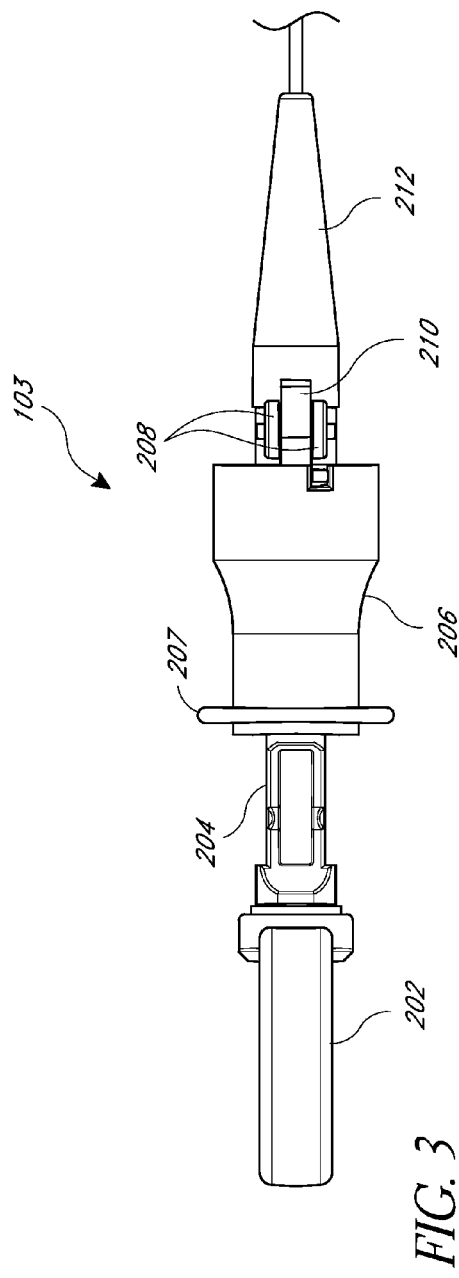
FIGS. 3-4 respectively illustrate top and bottom views of an embodiment of the handle portion of the catheter.
Figure 4:
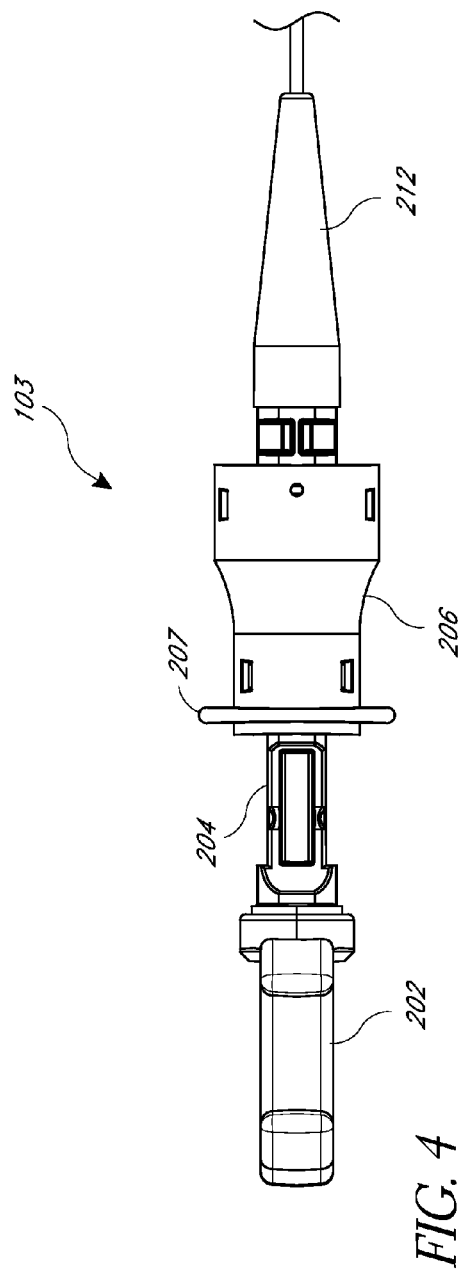

FIG. 1 illustrates an embodiment of a deployment catheter system 101. This system 101 comprises several different portions functioning together. A proximal end of the system 101 comprises a handle portion 103, which is coupled to a catheter shaft portion 105, terminating with a distal tip portion 107 at a distal end of the system 101. In a preferred embodiment, the proximal handle portion 103 is connected via the catheter portion 105 to the distal tip portion 107, which preferably contains a medical device to be deployed to a suitable site using the system 101. In some embodiments, the distal tip portion 107 may contain, or be configured to receive, a device such as a valve to be deployed in an airway passage.

FIGS. 2-5 illustrate additional exterior views of the handle portion 103. The handle portion 103 preferably is adapted to be held or gripped by a user, and comprises several parts. The handle portion 103 comprises a grip 202 that is connected to a plunger 204. A movable handle 206 is attached to, and may for example be disposed around, the plunger 204. The catheter shaft portion 105 is connected to the handle portion 103 at the distal end of the handle portion 103.

The grip 202 of the handle portion 103 may be constructed with a recess, which can permit the handle portion 103 to be held or engaged by the thumb of a user when about to deploy a device contained in the distal tip portion 107. As illustrated, the grip 202 may form a C-shaped grip. The grip 202 may take other shapes, for example but without limitation, the grip 202 may have an inner surface that is U-shaped, V-shaped, or recessed. In some embodiments, and as described below in further detail in FIG. 18B, the grip 202 may be attached to a device such as an endoscope, or more particularly a bronchoscope. The grip 202, as well as other parts of the system 101 that may be held or manipulated by the hand of a user, may be provided with a non-slip or rubberized coating to provide additional grip for a user.

The grip 202 is attached to the plunger 204. The plunger 204 may be provided with ergonomic finger knurlings 205 that can provide a more secure or comfortable grip for a user's fingers when operating the system 101.

The movable handle 206 is configured to movably engage with the plunger 204, such that the movable handle 206 can, for example, slide back and forth in a longitudinally axial direction along at least a portion of the plunger 204. From the position illustrated in FIG. 2, the movable handle 206 may move in a proximal direction toward the grip 202.

Distal to the movable handle 206, a securement tab 208 and a locking lever 210 may be attached to the plunger 204. The locking lever 210 is configured, when in the locked position illustrated, to engage with the movable handle 206 so as to reduce or eliminate the likelihood of the movable handle 206 moving in a proximal direction toward the grip 202. The movable handle 206 preferably comprises ergonomic aids, such as a ridge 207, that enable a user to easily manipulate and pull on the movable handle 206 during deployment of a medical device. In some embodiments, all or a portion of the movable handle 206 may be provided with a non-slip or rubberized coating to provide additional grip for a user.

The handle portion 103 may also comprise a strain relief component 212. Preferably, this strain relief component 212 couples to the handle portion 103 and is constructed from a resilient material, such as polymers including, for example but without limitation, rubber, thermoplastic elastomers (e.g., Santoprene™, Kraton®), polyurethane, polyvinyl chloride, PEBAX®, and silicone. The strain relief component 212 may be approximately conical or frustoconical in shape with a central opening extending lengthwise and configured to have close compliance with an outer sheath 316 (if so provided) or a catheter shaft 302 of the catheter shaft portion 105. The strain relief component 212 may reduce the likelihood of kinking or bending of the catheter shaft portion 105 near the point where the catheter shaft portion 105 meets the handle portion 103, and in particular when the catheter shaft portion 105 is inserted into instruments such as a bronchoscope and manipulated during use.

Figure 6:
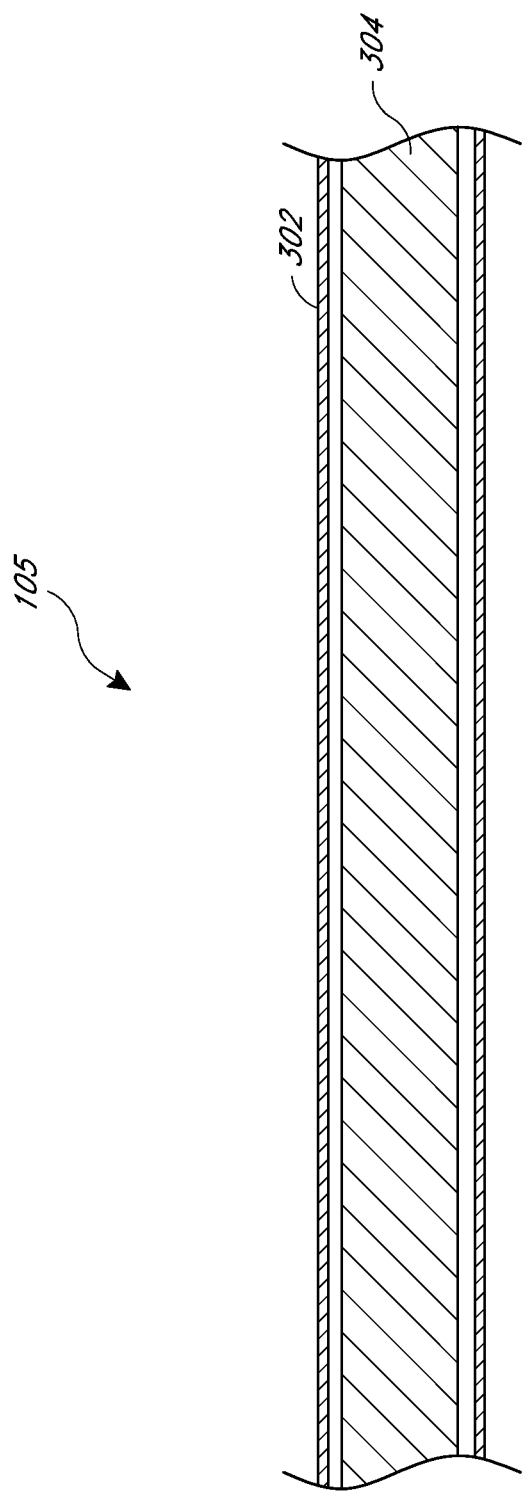
FIG. 6 illustrates a cross section of an embodiment of the catheter shaft.

With reference now to FIG. 6, a cross-section of the catheter shaft portion 105 is illustrated. The catheter shaft 302 is hollow and comprises a stabilization wire 304 extending longitudinally within it. The catheter shaft 302 preferably is constructed from a resilient and robust material, such as a metal or metals, that is resistant to elongation and plastic deformation while remaining flexible enough to be guided through tortuous passages and other similar constrictions. Suitable metals may include stainless steel, Nitinol, and the like. In some embodiments, polymer tubing may function satisfactorily, and embodiments may be manufactured, for example, from continuous polymer extrusions. These extrusions may also incorporate braids for additional strength and durability, and may be constructed from polymers such as polyimide. The stabilization wire 304 may likewise be constructed from similar materials.

In some embodiments, a lubricious coating or material may be added to either or both the stabilization wire 304 or the catheter shaft 302, which can aid the two parts in sliding past each other more freely and generally without binding or sticking. For example, polymers such as PTFE or parylene may be coated onto the stabilization wire 304. Coatings such as FEP can also be extruded onto the stabilization wire. Heat-shrink polymers such as PTFE or polyethylene may also be added to the stabilization wire 304.

In some embodiments, it may be preferable for the stabilization wire 304 to have a varying diameter along its length. This diameter may change, for example in a continuous or tapering manner, or in a stepwise manner. Without wishing to be bound by theory, it is believed that some embodiments of the stabilization wire 304 may benefit from having a thicker diameter at the proximal end (i.e., toward the handle portion 103) so as to reduce or eliminate the likelihood of buckling under higher applied loads, while having a thinner diameter toward the distal end (i.e., near the tip portion 107) so as to provide additional flexibility. In one embodiment, the stabilization wire 304 has a diameter of 0.020 inches from the proximal end until approximately one inch past an outer sheath 316. The remainder of the stabilization wire 304 has a stepwise change in diameter to 0.016 inches. This embodiment may be used in a catheter shaft 302 with an internal diameter of approximately 0.022-0.024 inches, such that the clearances on each side between the catheter shaft 302 and the stabilization wire 304 measure approximately 0.001-0.002 inches at the proximal end and 0.003 inches at the distal end.

With reference to FIG. 7, a cross section of the handle portion 103 is illustrated. FIG. 8 illustrates a close-up of this cross section. In a preferred embodiment, the grip 202 is connected to the stabilization wire 304, although in some embodiments the stabilization wire 304 may also or instead be connected to the plunger 204. The stabilization wire 304 is disposed within the catheter shaft 302, which preferably is configured to slide in a longitudinal direction over the stabilization wire 304.

In certain embodiments, a crimp tube 305 may be used to connect the stabilization wire 304 to the grip 202. The crimp tube 305 is preferably constructed from a metal, for example stainless steel alloys (e.g., SS304), that is harder than the stabilization wire 304 and formed as a hypotube. Preferably, the crimp tube 305 is crimped over the proximal end of the stabilization wire 304, with the proximal end of the crimp tube 305 being held within the grip 202 and the distal end of the crimp tube 305 being held within the remainder of the body of the plunger 204. In some embodiments, the crimp tube 305 may extend partially over the catheter shaft 302, for example for a short length of 0.1 inches, as this may provide additional buckling resistance to the catheter shaft 302 when forces are applied to the catheter shaft 302. In some embodiments, the crimp tube 305 may have an internal diameter measuring approximately 0.039 inches, with a wall thickness of 0.010 inches.

The catheter shaft 302 is connected via a fork 216 to the movable handle 206. Because the movable handle 206 preferably is configured to slide back and forth along the plunger 204, and because the movable handle 206 is coupled to the catheter shaft 302, movement of the movable handle 206 will cause a corresponding movement of the catheter shaft 302 in relation to the stabilization wire 304. As will be discussed below, this movement may permit ejection and deployment of a device loaded in the distal tip 107. Further, the locking lever 210 may be provided with a locking tab 222 that engages with a recess 220 on the movable handle 206, thus helping reduce or eliminate the likelihood of the movable handle 206 from sliding along the plunger 204. Such a provision can be used to help reduce or eliminate the unintended or premature deployment of a device from the catheter system 101. In certain embodiments, the catheter shaft 302 could instead be connected to the plunger 204, and the stabilization wire 304 could be connected via the fork 216 to the movable handle 206.

Figure 9A:
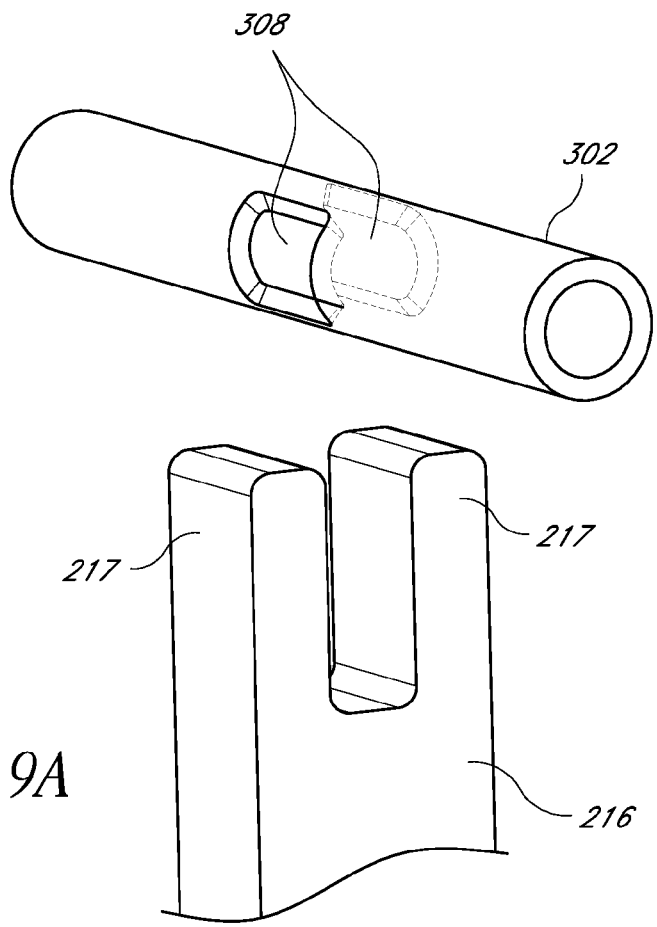
FIGS. 9A-B illustrate close-up views of a fork attaching the catheter shaft onto an embodiment of a catheter handle.
Figure 9B:
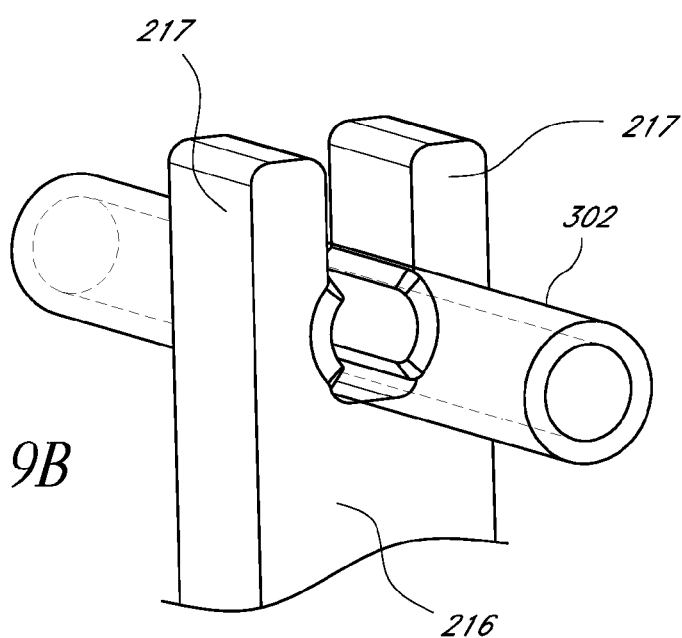

The catheter shaft 302 preferably is secured to the handle portion 103, and in certain embodiments one or more intermediate components may form part of this connection. In some embodiments, and with reference now to FIGS. 9A-B, the catheter shaft 302 may be secured to a fork-shaped intermediate component such as a fork 216, and may for example be held in a recess in the fork-shaped intermediate component. This fork 216 is in turn connected to the movable handle 206. The movable handle 206 is omitted for clarity, but its relation to these other parts can be seen in FIGS. 7-8.

The fork 216 preferably comprises at least two prongs 217. These prongs 217 have a space in between each other that is less than the diameter of the catheter shaft 302. In order to connect the catheter shaft 302 to the fork 216, the catheter shaft 302, which preferably is constructed with a circular cross-section, may therefore have one or more indents or cavities 308 formed thereon. This indent or cavity 308 permits the catheter shaft 302 to be received in the space between the two prongs 217, as the cavities 308 will, at that distance along the catheter shaft 302, cause the catheter shaft 302 to have a smaller cross-sectional distance so as to permit the catheter shaft 302 to be inserted and secured in the space between the two forks 217. Accordingly, an axially secure connection can be made between the catheter shaft 302 and the fork 216. As the stabilization wire 304 lies inside the catheter shaft 302, care must be taken that the indents or cavities 308, 310 do not substantially interfere with the relatively free movement of or cut into the catheter shaft 304.

Tests have shown that an embodiment of the fork 216 constructed from stainless steel (the fork 216 may be constructed from any suitable rigid material, for example metals including stainless steel) could withstand a force greater than 20 pounds before failure. Because a user is unlikely to be able to apply this much force during deployment, this construction makes it more likely that the system 101 will remain intact, and that failure of the fork 216 is thus less likely to cause the catheter shaft 302 to detach from the remainder of the system 101.

Referring back to FIG. 1, an outer sheath 316 may also be provided over the catheter shaft portion 105. The outer sheath 316 may be disposed between the catheter shaft 302 and the strain relief component 212, and may serve (in addition to the strain relief component 212, if so provided) to minimize kinking and torsional loading of the catheter portion 105. To ensure secure connection of the sheath 316, it may be preferable to secure the sheath 316 to the plunger 204, for example by insert molding or adhesives. In some embodiments, the outer sheath measures between 22 and 39 inches, with a wall thickness between approximately 0.005-0.015 inches, preferably 0.010 inches. Preferably, the outer sheath 316 has a gap or clearance between itself and the catheter shaft 302. In some embodiments, this clearance measures approximately between 0.003-0.010 inches, preferably 0.005 inches per side. In some embodiments configured to be sterilized (e.g., using ethylene oxide gas sterilization), the clearance between the catheter shaft 302 and the outer sheath 316 may be designed to permit adequate flow of sterilant between the two parts.

The outer sheath 316 preferably is constructed from materials including polymers such as HDPE, Nylon-12, PEBAX®, polyurethanes, or blends thereof, for example in a single polymer extrusion. In some embodiments, the outer sheath 316 is co-extruded with two different materials. On the side of the outer sheath 316 facing the catheter shaft 302, a lubricious material may be used, for example HDPE, FEP, or another suitable material. On the outer side of the sheath 316, a polymer such as PEBAX® or Nylon-12, or another suitable material may be used to achieve a balance between factors such as pushability (e.g., limiting the amount of force a user can apply), mechanical strength (e.g., resistance to yielding while under load), kink resistance, friction with the inside of the bronchoscope, and manufacturability. In some embodiments, radioopaque materials, for example barium sulfate, may be incorporated into the sheath 316 and/or other elements of the catheter system 101.

Figure 10A:
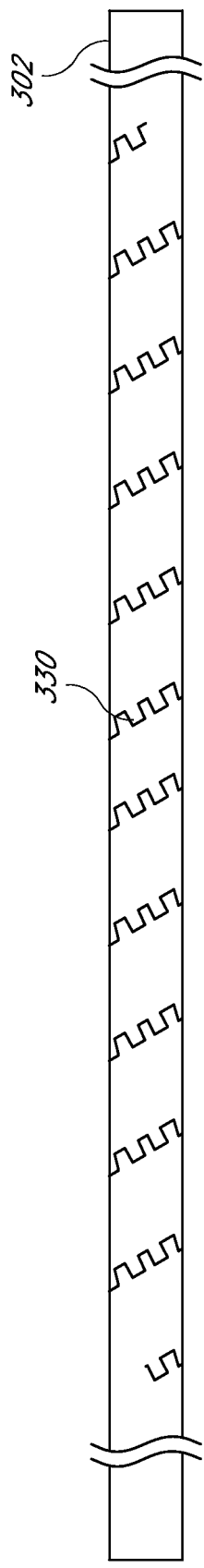
FIGS. 10A-C illustrate embodiments of a high flexibility region present on a catheter shaft.
Figure 10B:
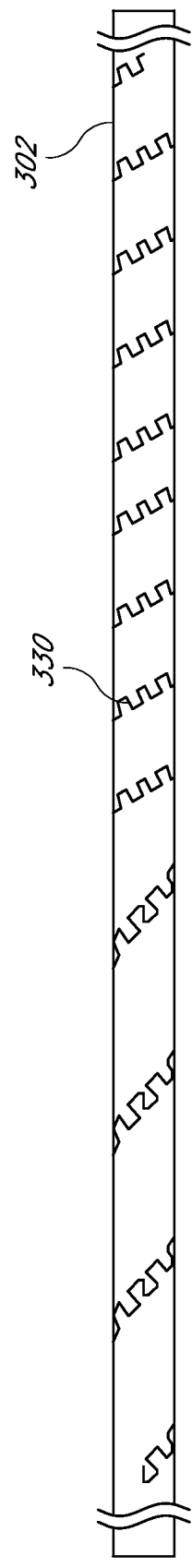
Figure 10C:
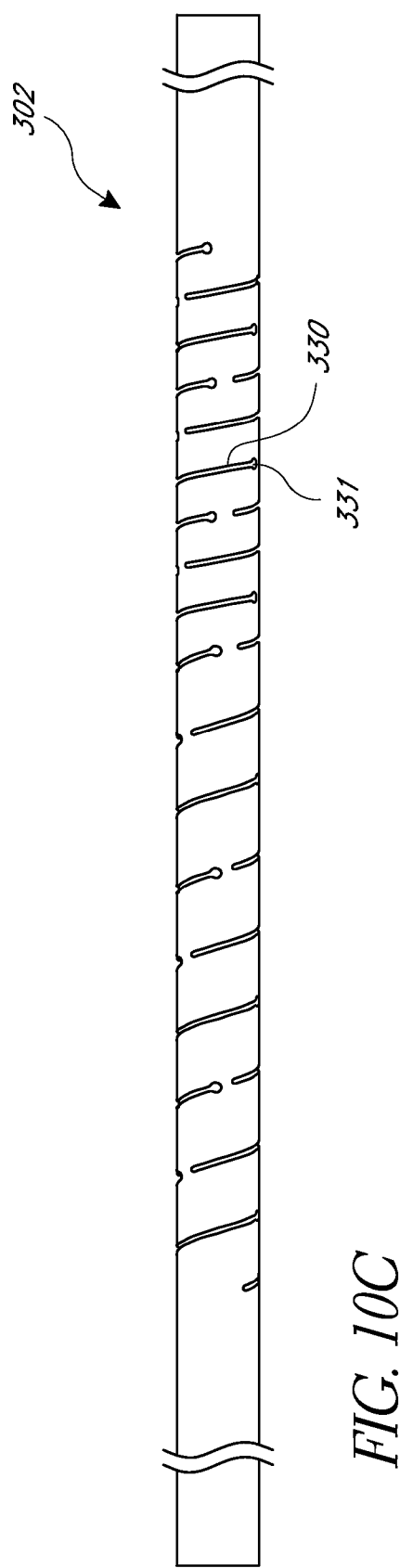

With reference to FIGS. 10A-C, a series of cuts may be made along substantially all or part of the catheter shaft 302. These cuts may define one or more regions 330 of increased flexibility that are typically able to bend or flex better than a catheter shaft 302 left uncut. In some embodiments, it has been found that the catheter system 101 performs well if a portion of the distal end of the catheter shaft 302 has a high flexibility region 330 cut into it, as the distal portion of the catheter shaft 302 may need to be bent to a greater extent in order to navigate tortuous airway passages, for example. The flexibility of the high flexibility region 330 may be tailored as desired for a particular application. The flexibility can be changed, for example, by modifying the thickness of the catheter shaft 302, the materials used therein, and the spacing, pitch, and angle between the cuts in the high flexibility region 330. Preferably, the cuts extend in a spiral fashion along the catheter shaft 302.

Additionally, the high flexibility region 330 does not need to be of the single pitch illustrated in FIG. 10A, but, with reference to FIG. 10B, can instead be of a variable pitch, wherein the spacing or pitch can be changed in a continuous or stepwise fashion. Additionally, although the cuts shown in these figures are made in a continuous and single cut, high flexibility regions may be made using one or more discontinuous cuts. In these figures, the cuts that constitute the high flexibility region 330 are made in a "jigsaw" configuration that forms a sawtooth or zigzag pattern. Other possible cuts are a "serpentine" configuration as illustrated and discussed below in FIGS. 16B and C. In this serpentine configuration, the cuts are smoother, more rounded, and with a longer amplitude than the jigsaw pattern. Other cut types are possible and envisioned, including straight cuts, partial or dashed cuts, zigzag cuts, sinusoidal cuts, and so on.

FIG. 10C illustrates an embodiment of a high flexibility region 330 comprising overlapping discontinuous straight cuts, each extending around approximately half of the circumference of the catheter shaft 302. In this embodiment, punch holes 331 may be provided at one or more of the ends of each cut. The punch holes 331 may in some cases be made as part of a laser cutting process used to create the cuts, although the cuts may be made using any suitable process, for example chemical etching. Punch holes 331 may also be useful in providing additional strength to the catheter shaft 302, as it is believed that the punch holes 331 may aid in reducing or eliminating the likelihood of crack propagation when the catheter shaft 302 undergoes various stresses.

In practice, tailoring of the high flexibility region 330 and the cuts that constitute this high flexibility region 330 may be desirable to find the right balance between the flexibility required and the type of cut. For example, while wider or larger cuts may provide additional flexibility, these may in some cases weaken the catheter shaft 302 to an unacceptable extent. Different cut types may also perform more or less satisfactorily in fatigue testing. Additionally, certain cuts may cause portions of the high flexibility region 330 to abrade the working channel of the bronchoscope, although postprocessing after creation of the cuts may include steps such as deburring or ultrasonic cleaning which may at least partially alleviate such concerns. The type of cuts described above may also be adjusted in accordance with the length of the one or more high flexibility regions 330.

In preferred embodiments, high flexibility regions 330 measuring 3 to 6 inches, with the pitch between cuts measuring between 0.010 to 0.100 inches, have been found to work well. The cut width (kerf) has been found in some embodiments to be satisfactory in the range between 0.0015-0.0030 inches.

In certain embodiments, it may be preferable to cover at least the high flexibility region 330 with a flexible protective layer, for example a polymer or heat-shrink material. Such a protective layer can at least partially mitigate abrasion of the interior of the working channel of a bronchoscope due to the cuts and also reduce or eliminate the likelihood of damage or overstretching of the catheter shaft 302, which may aid in making the catheter usable for multiple deployments. Additionally, this protective layer may also be lubricious or lubricating, thus permitting the catheter shaft 302 to slide more easily within a bronchoscope working channel.

With reference now to FIGS. 11A-B and 12A-B, the distal tip portion 107 may be joined to the catheter shaft portion 105 via a connector 402. More specifically, in some embodiments this connector 402 connects the outer catheter shaft 302 to the distal tip portion 107. In a preferred embodiment, the distal tip portion 107 may comprise a cage 404, the cage 404 being connected to the catheter shaft 302 via the connector 402. This cage 404 may be constructed from a sufficiently durable material or materials, including metals such as stainless steel and Nitinol. In some embodiments, the cage 404 may be constructed from pre-formed tubing, and some other embodiments may have the cage 404 constructed from a flat portion of material which is then wound to form a tube, either in a lengthwise or spiral direction.

The distal tip portion 107 preferably is configured to contain a cavity 405 disposed within it, the cavity 405 being sized to contain a suitable device to be subsequently deployed. Preferably, the cage 404 comprises the cavity 405 disposed in a space within the cage 404.

Figure 11A:
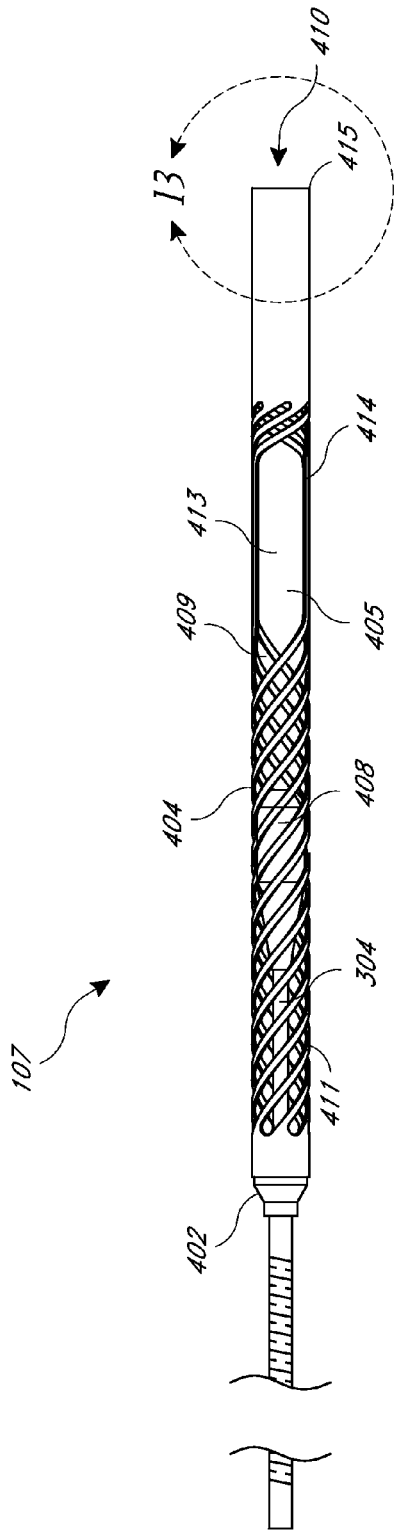
FIGS. 11A-B respectively illustrate close-up views of an embodiment of the distal tip of the catheter without and with a valve loaded therein.
Figure 11B:
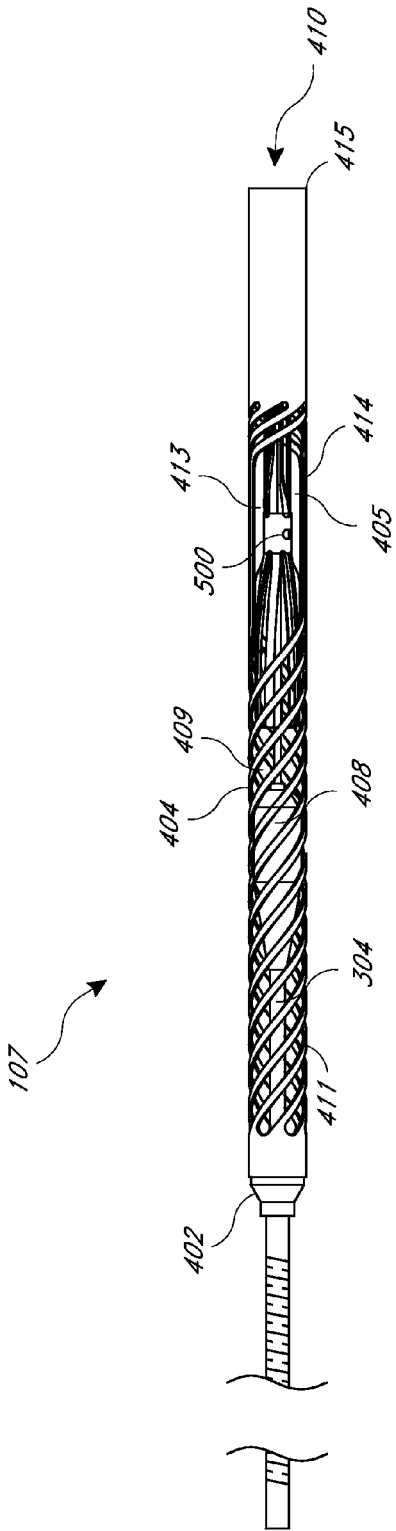

In some embodiments, and as illustrated in FIGS. 11B and 12B, the cavity 405 may contain a medical device such as a valve 500. In such cases, the valve 500 may be loaded into the cavity 405 through the distal opening 410 by using a valve loader apparatus of the type described in U.S. Ser. Nos. 12/249,243 and 12/422,179, each of which is hereby incorporated in its entirety. Once loaded into the cavity 405, the proximal end of the device (for example the valve 500) abuts against a pusher plunger 408, which is in turn connected to the stabilization wire 304. In use, proximal motion of the movable handle 206 in relation to the plunger 204 in the handle portion 103 causes the cage 404 to retract relative to the pusher plunger 408, thereby releasing the device (such as valve 500) contained in the cavity 405 from the opening 410.

Fenestrations 409 are preferably disposed on at least a portion of the cage 404, and may serve the purposes of improving visibility of a device disposed therein as well as improving flexibility of the distal tip portion 107. The remaining struts 411 form a cage or frame-like structure, and may comprise a spiral or staggered spiral pattern, although different configurations and patterns are possible. The fenestrations 409 may be, for example, laser-cut. Other methods, such as photochemical milling, may also be employed.

Preferably, the cage 404 also contains one or more large fenestrations 413. This large fenestration 413 may be useful in visualizing a device disposed within the cavity 405, as well as confirming that a device has been properly or correctly loaded in the cavity 405. The large fenestration 413 may also be useful in providing a clear area for locating a marker band or other localization marker (discussed in further detail below). Preferably, the entire cage 404 is constructed from a single piece of material, and the distal portion of the cage 404 comprising the rim 415 may be connected to the proximal section of the cage 404 via longitudinal struts 414.

In the manufacture of the distal tip portion 107, it may be advantageous to coat inner and/or outer portions of the distal tip portion 107 and the cage 404. For example, coating with a softer material, for example a polymer, may be useful to avoid injury to bodily tissue when using the catheter, as well as helping the distal tip portion 107 to slide freely within the working channel of a bronchoscope or other instrument. Additionally, coating the inner portion of the catheter may help in reducing or eliminating the likelihood of damage to a medical device loaded therein, or snagging of the medical device during deployment.

Thus, certain embodiments provide for providing a liner, consisting for example of a polymer such as polytetrafluoroethylene, disposed on at least a portion of the inner surface cage 404 or cavity 405, in combination with a liner disposed on at least the outer surface of the distal tip 107 portion, which may consist of a polymer such as PEBAX®.

In some embodiments, these coatings or liners may be reflowed onto the distal tip portion 107. Using a mandrel, heating may be applied to reflow these liners over the metal portion of the distal end 302. Preferably, the liners chosen are at least partially transparent over the fenestrations 409, 413 such that a medical device loaded therein can be inspected. Different polymers and polymer types may be used along different portions of the distal tip 107, where for example a transparent polymer is used along only one portion of the distal tip 107, while an opaque or pigmented polymer is used along a different portion of the distal tip 107, permitting the catheter to be specifically tailored to the desired application and use. As discussed below and in FIG. 15, such polymer coating and reflowing may also incorporate localization markers onto or into the distal tip portion 107. Different methods may be used to coat the distal tip portion 107, including dip coating, extrusion, applying heat shrink materials, and so on.

In a preferred embodiment, the rim 415 surrounding the opening 410 located at the distal end of the distal tip portion 107 is configured to be smooth and atraumatic, so as to reduce or eliminate the likelihood of injury to body tissue during insertion and deployment of a device located in the cavity 405.

Figure 13:
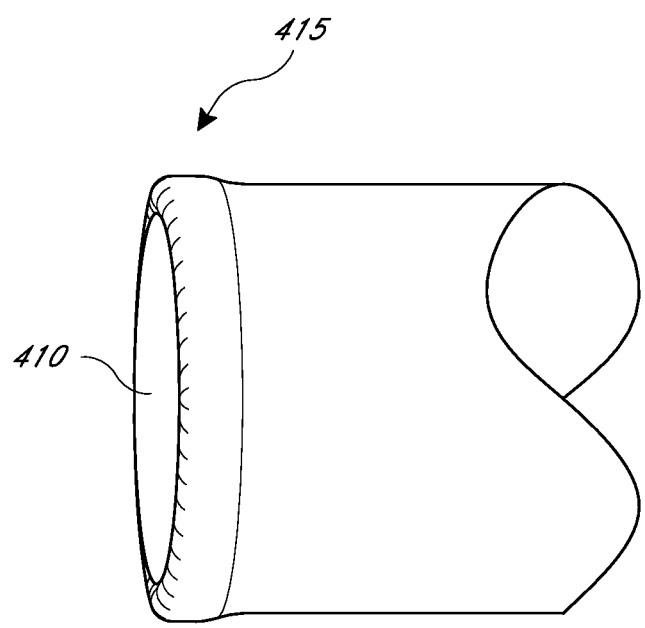
FIG. 13 is a close-up view of the extreme end of the distal tip of an embodiment of the catheter.

Preferably, and with reference to FIG. 13, the rim 415 comprises a series of small welds arranged circumferentially around the opening 410, and which may for example be made using laser welding so as to provide a smooth, rounded end. In such a case, the rim 415 may thus be configured to provide an atraumatic tip that minimizes snagging or other engagement with a device that may be deployed from the cavity 405, while also being durable and capable of sustaining multiple uses. In other embodiments, the rim 415 may be covered with a layer of polymer or other soft material.

Referring back now to FIGS. 11A-B and 12A-B, in some embodiments the connector 402 may be seam-welded along the boundary joining the connector 402 to the distal tip portion 107, via either the cage 404 or the distal end of the catheter shaft 302. Such a weld is preferable as it provides for a smoother transition from the catheter shaft portion 105 to the distal tip portion 107, thereby reducing operator effort and helping provide for smooth, continuous movement of the system 101 during deployment. Spot-welding may be used as well, although care should be taken to reduce the size of the spot weld from excessive protrusion, as there could be a risk that such a weld may catch or snag within a bronchoscope.

Figure 14:
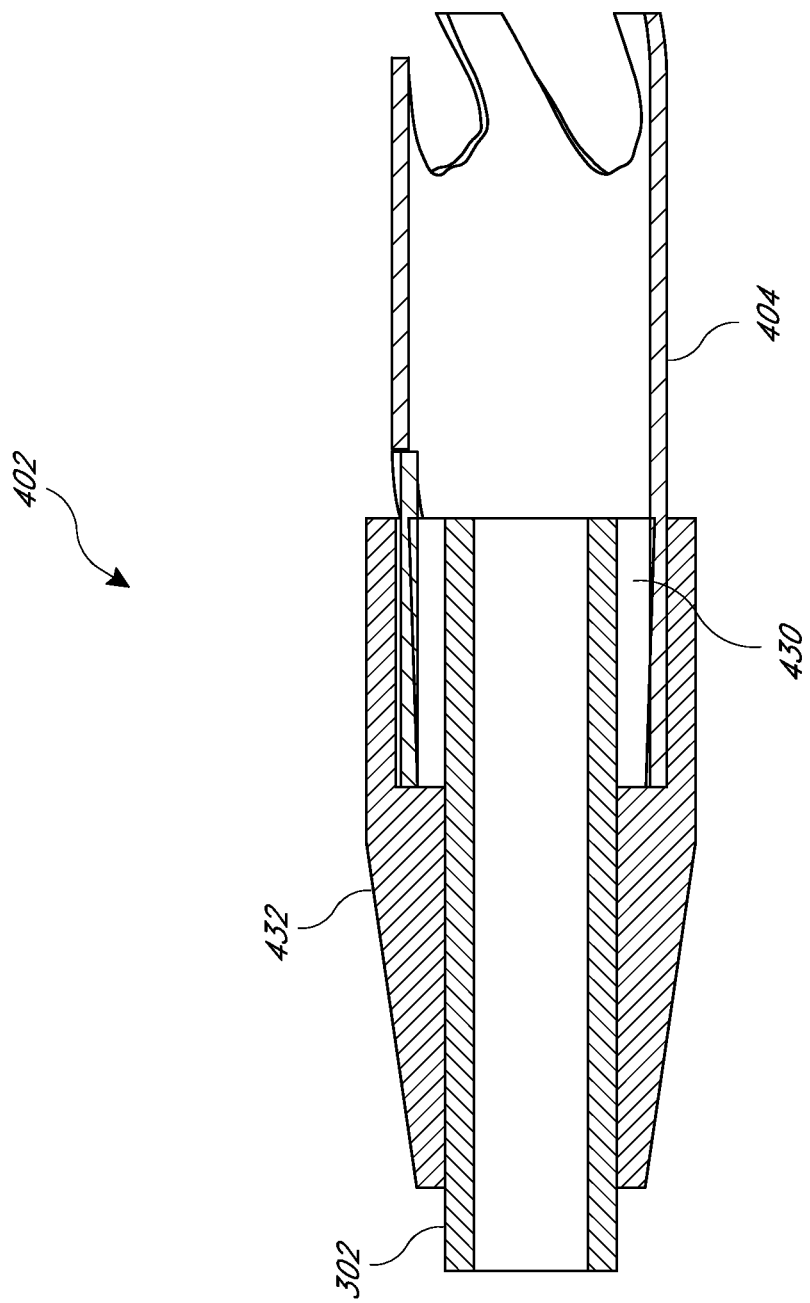
FIG. 14 illustrates an embodiment of a connector mechanism that may be used to attach a distal tip to a catheter shaft.

With reference to FIG. 14, certain embodiments may provide for the connector 402 to be constructed from a multi-part design. In such embodiments, a compression cone 430 is attached, for example by welding, to the distal end of the outer catheter shaft 302. A ferrule 432 is attached, for example by welding or simply through mechanical interlocking, to the distal end 402, which may then be pushed over the compression cone 430 so as to sandwich the proximal end of the cage 404. This interlocking connection comprises connector 402, and forms a strong connection capable of resisting most pulling forces. Samples have been tested to withstand a pulling force of at least 100 N.

Figure 15:
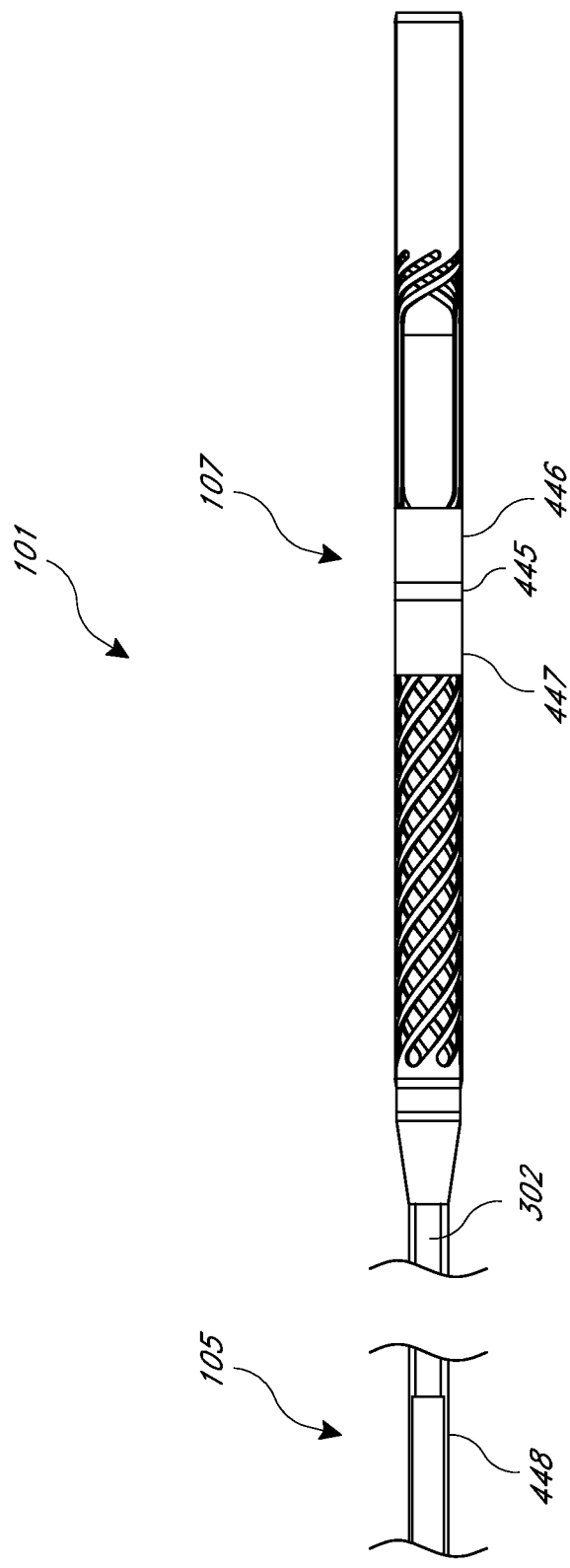
FIG. 15 illustrates a close-up view of a distal tip of an embodiment of the catheter shaft with locator markings added thereto.

Turning now to FIG. 15, an embodiment of the system 101 may be provided with localization markers. These localization markers may be provided, for example, on parts of the distal tip portion 107 and the distal end of the catheter shaft portion 105. Generally, localization markers aid an operator in ascertaining the position of the system 101 in relation to external objects. The localization markers may be visual, and may thus be useful while in a limited-visibility environment such as the field of view as seen through a bronchoscope. More specifically, localization markers may be helpful for selecting and indicating an appropriate deployment site for a medical device loaded in a catheter, and may also be useful in allowing an operator to determine if a catheter has been extended too far out of, for example, a bronchoscope's working channel or other delivery device.

Certain embodiments may be provided with one or more localization markers, such as lines 445, 446, 447, which may aid in selecting and indicating an appropriate deployment site for a medical device loaded into the catheter. Here, when the catheter containing a device is loaded into a bronchoscope and guided to a portion of the body requiring treatment (for example a lung airway), an operator may use the line 445 to align the catheter with the site where the medical device is to be deployed, as the line 445 will denote the approximate location where the medical device will be released from the opening 410. In some embodiments, the device may be a valve 500 for deployment in an airway, and in such cases, the line 445 will generally align with the air passageway region that the membrane of the valve 500 will seal against. These embodiments are described in further detail below and in FIGS. 20A-C.

The line 445 may be particularly useful to aid in visualization of an appropriate deployment site through a bronchoscope viewing channel, and some embodiments provide for the line 445 to be surrounded or flanked by additional black or differently-contrasting bands of color 446, 447 to provided additional contrast. Although the line 445 may be marked on the distal tip portion 107 with any appropriate means, such as pad printing or inkjet printing, biocompatibility concerns may sometimes necessitate that the line 445 not employ exposed pigments in its construction. In such cases, some embodiments may use a marker band placed around the distal tip portion 107. Such a marker band may consist of a polymer band, for example constructed from a heat-shrinkable polymer such as PEBAX®. As a yellow line 445 has been found to be advantageous in certain applications, a gold-colored marker band may be slipped onto the distal tip portion 107. The marker band may be composed from any suitable material, and preferably is highly visible. Materials such as gold or platinum with iridium are materials that have been found to be acceptable. Optionally, a marker band serving as a line 445 may be encapsulated below the liner described in the reflowing process above, or may be encapsulated under an additional and preferably at least partially transparent layer of polymer, such as PEBAX®.

In some embodiments, the line 445 or other localization markers may be formed by cutting a line or series of perforations into the distal tip portion 107, such that no additional materials are required to form the respective localization markers. Further, although the line 445 is described above as being disposed on the distal tip portion 107, other embodiments may place the line 445 on other portions of the system 101. For example, a line 445 may be made on the stabilization wire 304 or plunger 408, with an associated aperture or window cut into the distal tip portion 107 if necessary to permit visualization of the line 445.

In addition, certain embodiments may provide for a long localization marker 448 disposed, for example, on a distal portion of the catheter shaft 105. This long localization marker 448 may be used as a warning feature to an operator that the catheter system 101 has been extended too far past the bronchoscope. This long localization marker 448 preferably is pigmented or colored, for example in a contrasting color such as yellow, so as to be readily visible by an operator should the catheter be extended past the bronchoscope. The long localization marker 448 may be placed onto the catheter shaft 105 using any suitable means, including the ones described previously for the lines 445, 446, 447. Preferably, the long localization marker 448 may be constructed from a suitable heatshrink polymer, which may in some cases be subsequently covered by a clear or unpigmented protective polymer layer. In some embodiments, the long localization marker 448 may measure between 5 and 10 inches, and preferably six inches, and may be located approximately two inches from the distal tip.

Although the localization markers discussed above refer primarily to visual indicators, localization markers used in the system 101 may be configured for localization using other means. For example, any of the localization markers or lines 445, 446, 447, 448 may be constructed from or incorporate a radioopaque material (e.g., barium sulfate) for localization using radio imaging methods. In an MRI-compatible embodiment of the system 101, MRI contrast agents could also be incorporated into the localization markers. Active (powered) or passive (e.g., passive RFID) localization beacons may also be incorporated into the distal tip portion 107, which may function in addition to or to replace the localization markers discussed above, and which could function in conjunction with mapping software so as to track the location of the distal tip portion 107 in real time and without necessarily requiring visual confirmation of the position of the distal tip portion 107 with respect to a deployment site. These localization markers may also be hybrid localization markers combining multiple localization methods, such as localization markers that are both radioopaque and visual.

Figure 16A:
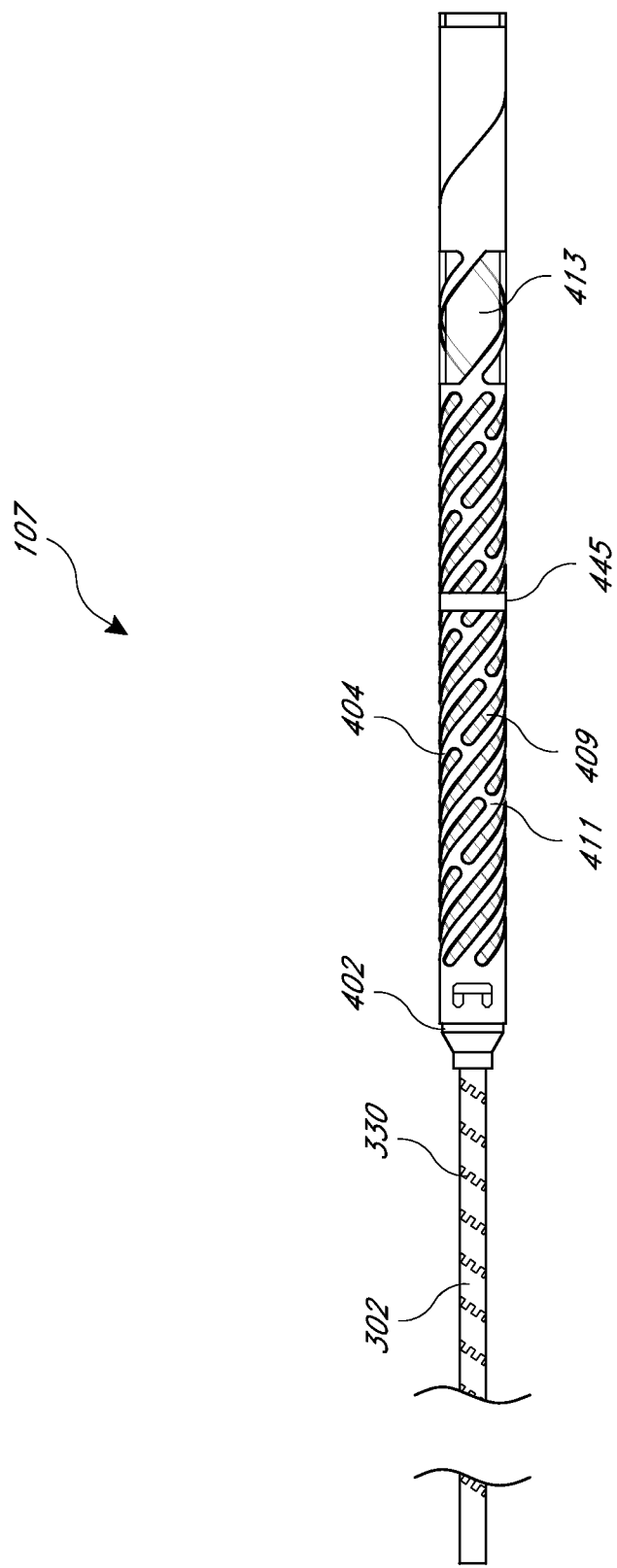
FIGS. 16A-H illustrate various embodiments of a distal tip of the catheter.

FIGS. 16A-H illustrate different embodiments of the distal tip portion 107. Although these designs may share several similarities with FIGS. 11A-B and 12A-B, additional differences and features will be discussed herein. Turning first to FIG. 16A, an embodiment of the distal tip portion 107 is shown that comprises a staggered spiral configuration in the cage 404 (as contrasted with the continuous spiral or helix configuration illustrated in FIGS. 11A-B). The additional material present, and which links the struts 411 together, may provide added strength against external and internal forces that may be applied to the tip while in use (e.g., torsional or bending forces). In a preferred embodiment, the cage 404 may be constructed from a sheet of Nitinol, chemically etched, and rolled to a cylindrical shape.

Additionally, the connector 402 is provided here with a multi-part connector similar to that described above in relation to FIG. 14. Localization markers including line 445 may also be present. As discussed previously, this embodiment comprises a high flexibility region 330 with a jigsaw cut configuration on the catheter shaft 302.

Figure 16B:
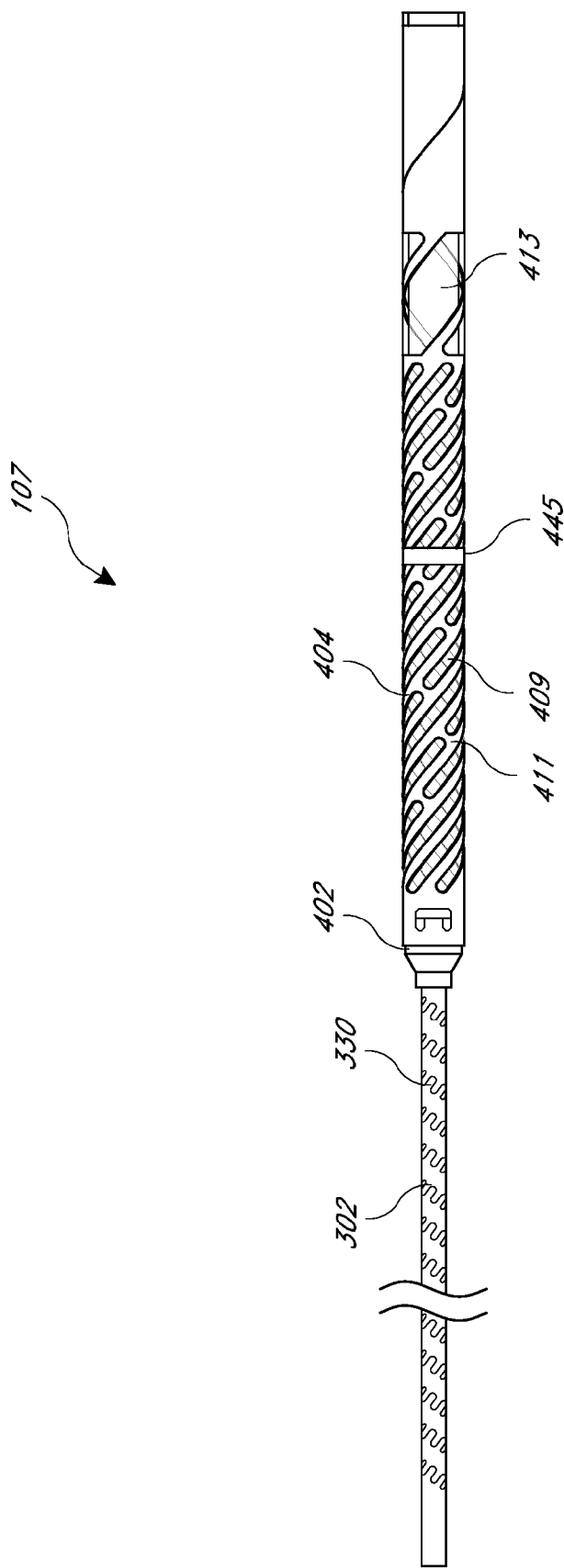

FIG. 16B illustrates a similar embodiment with a different high flexibility region 330 on the catheter shaft 302, this time formed in a serpentine design.

Figure 16C:
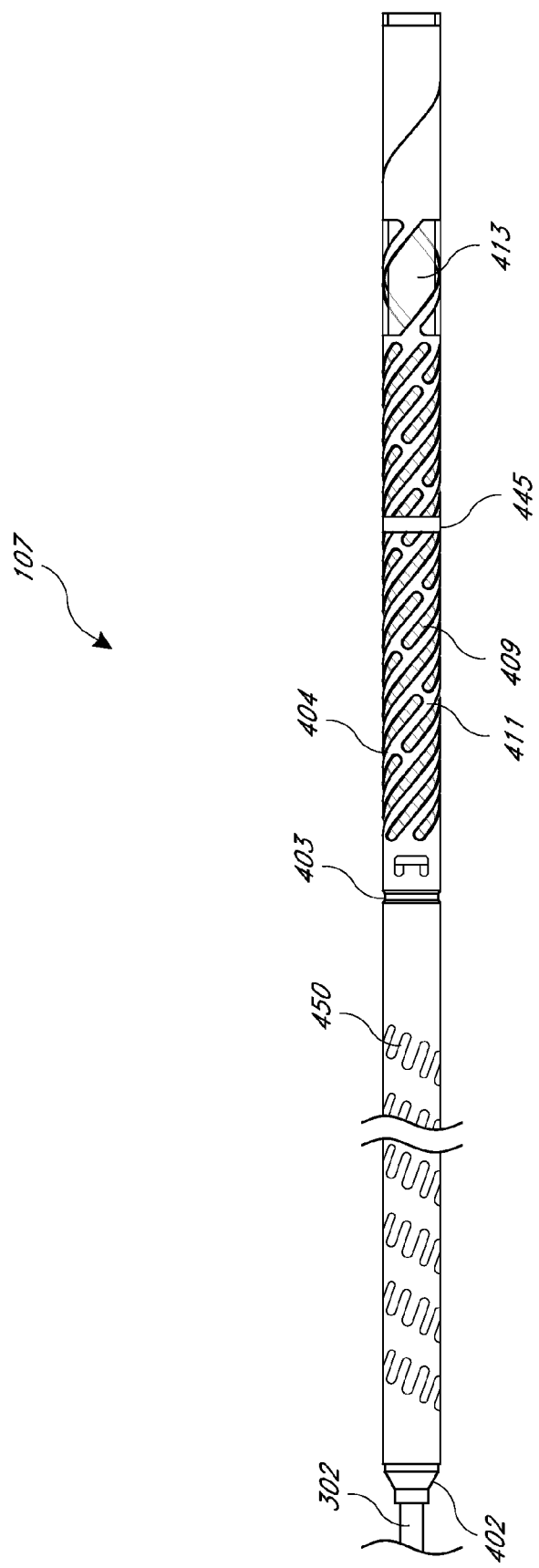

Turning now to FIG. 16C, this embodiment comprises a high flexibility region 450 that has been integrated onto the distal tip portion 107 and is otherwise similar to the high flexibility region 330 illustrated in FIG. 16A, except that the region 450 here is on the distal tip portion 107. The high flexibility region 450—here, made in a serpentine cut configuration—connects to the catheter shaft portion 105 via a connector 402, and connects to the cage 404 via a second connector 403. Additionally, some applications may entail adding another additional high flexibility region 330 of the type previously described in addition to the high flexibility region 450 illustrated here to the catheter shaft 302. In some cases, the interior of the high flexibility region and/or the cage region may be lined with PTFE or other lubricious polymers to minimize buckling of the stabilization wire that extends through the finished catheter.

Figure 16D:
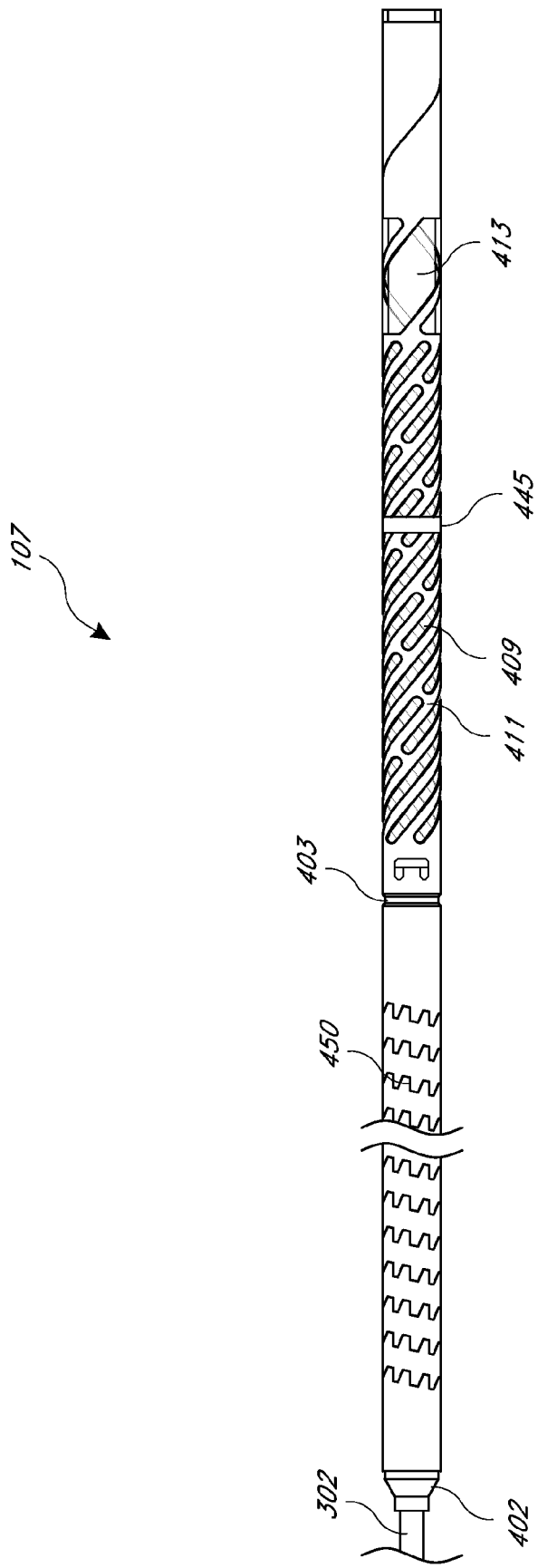

FIG. 16D illustrates another embodiment of the distal tip portion 107 that is similar to the embodiment described in FIG. 16C. Here, the high flexibility region 450 comprises a jigsaw design.

Figure 16E:
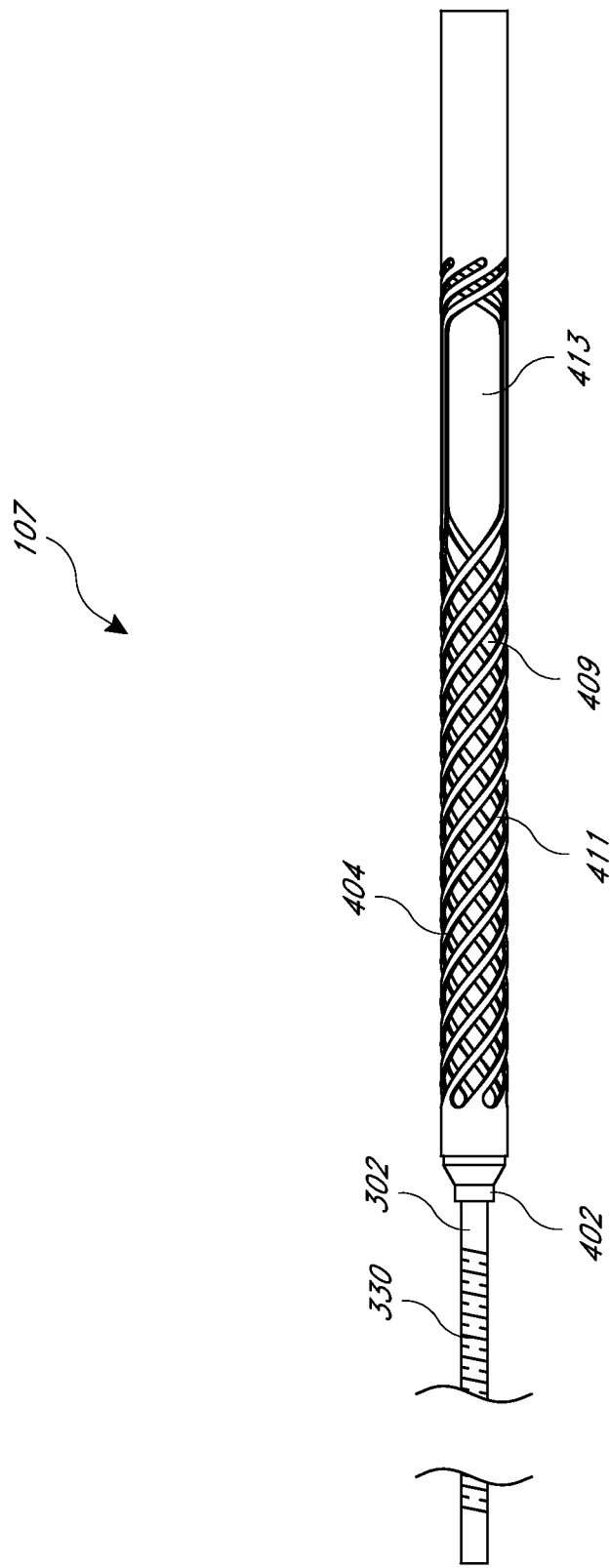

FIG. 16E illustrates an embodiment of a distal tip portion 107 similar to the embodiment illustrated in FIG. 11A, with the cage 404 comprising a spiral configuration. Here, the high flexibility region 330 disposed on the catheter shaft 302 comprises overlapping discontinuous straight cuts, each extending around approximately half of the circumference of the catheter shaft 302. These cuts may be similar in configuration to those illustrated in FIG. 10C. Because these cuts are discontinuous, some embodiments of the resulting high flexibility region 330 may have additional strength compared to other high flexibility region types illustrated herein.

Figure 16F:
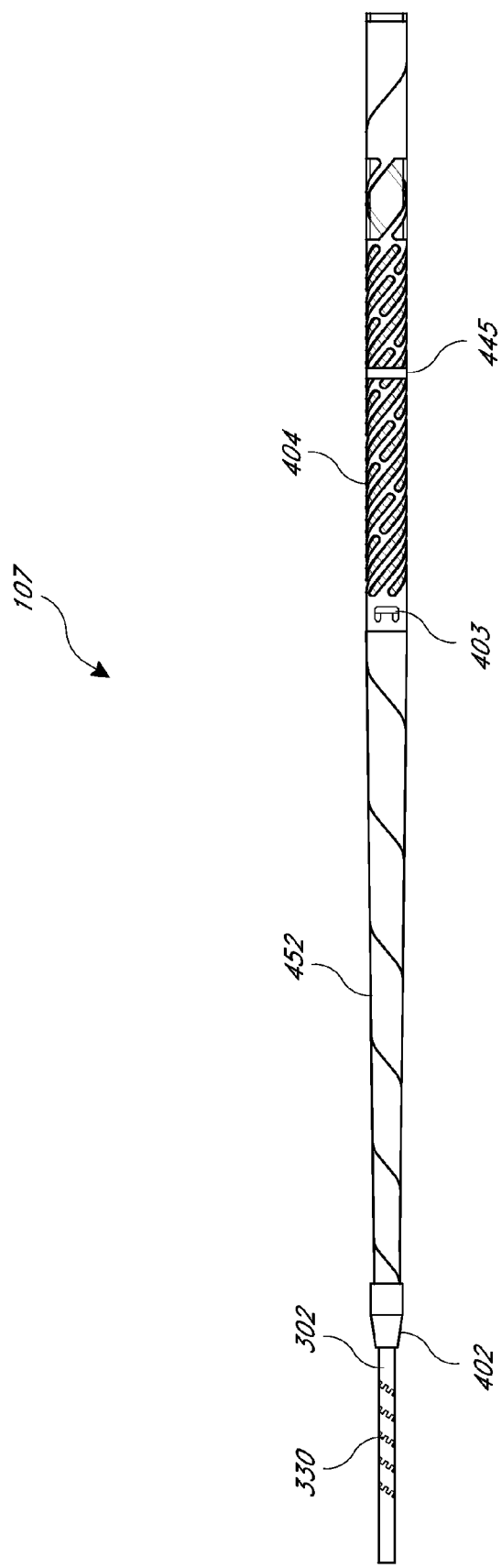

FIG. 16F illustrates an embodiment of the distal tip portion 107 that comprises a tapered portion. Here, the cage 404 is connected via a second connector 403 to a tapered portion 452 which tapers to a smaller diameter toward its proximal end. The tapered portion 452 is connected to the catheter shaft 302 via a connector 402, and may be provided with a high flexibility region 330 similar to those previously described. In some embodiments, the tapered portion and/or the cage may be formed by producing a helical wrap from sheet stock of a rigid material such as Nitinol that has been photochemically etched (although different metals or materials may be employed). Some advantages of this tapered embodiment may include smoother movement of the catheter system 101 through a bronchoscope working channel.

Figure 16G:
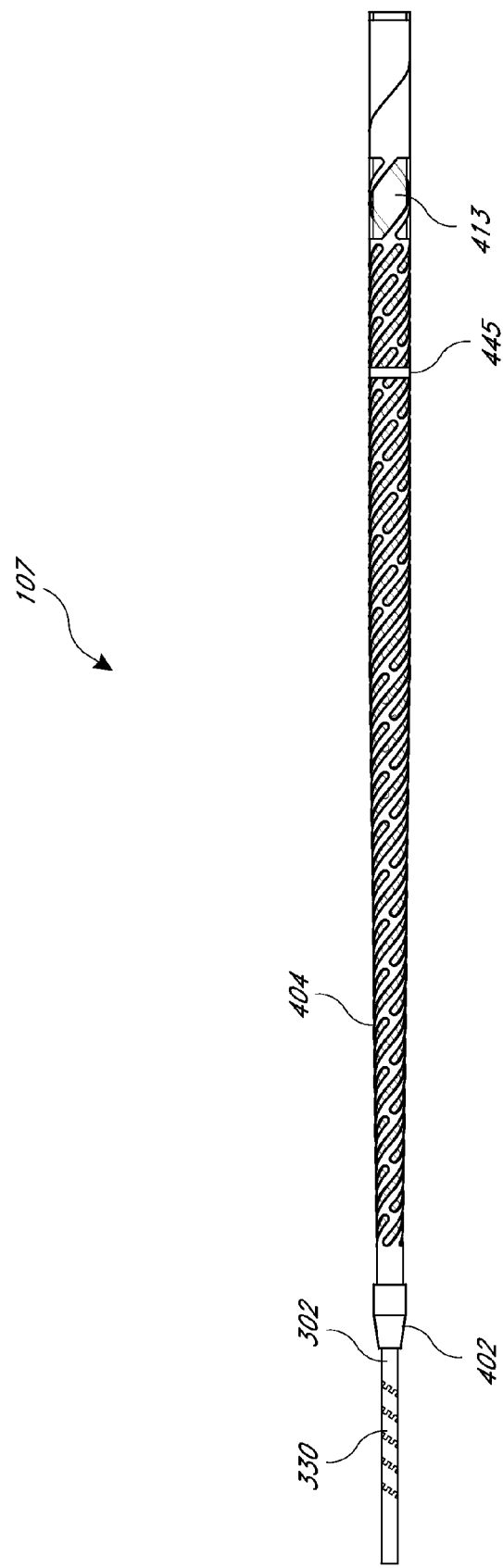

FIG. 16G illustrates another embodiment of the distal tip portion 107 that comprises a different tapered portion. Here, the cage 404 itself is formed as a single unit (contrasted with FIG. 16E) and tapers to a smaller size toward its proximal end. Such a cage design may be in some cases cheaper to manufacture and assemble compared to the multi-piece design of FIG. 16E, and may in some cases be photochemically etched from a single sheet of nitinol, and subsequently rolled to shape. This single piece tapered embodiment may also be manufactured so that the staggered spiral configuration illustrated here does not extend as far proximally as illustrated here, so that such an embodiment may resemble the embodiment illustrated in FIG. 16F without a second connector 403.

Preferably, the cage 404 is attached to the catheter shaft portion 105 using a connector 402 of the type described above in FIG. 14. As with FIG. 16F, a high flexibility region 330 (here, of the "jigsaw" type) may be present on the catheter shaft 302.

Figure 16H:
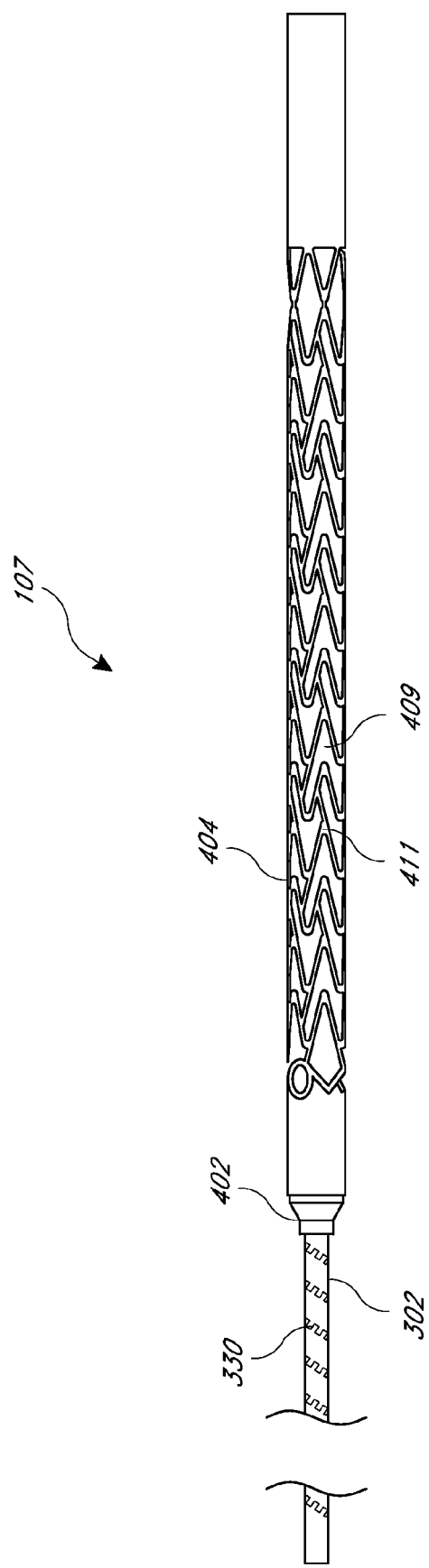

FIG. 16H illustrates a different configuration for the cage 404 that may be used in certain embodiments of the distal tip portion 107. Here, rather than a spiral or helical configuration, the cage 404 may be formed with a braided configuration as illustrated. Such a configuration preferably is laser cut, although different manufacturing methods such as photochemical milling are also possible. The configuration of this embodiment of cage 404 may be advantageous in applications requiring additional flexibility in the distal tip region 107. In some configurations, for example when the cage 404 is constructed from nitinol, a nitinol compression ring may be used to secure the cage 404 to the catheter shaft portion 105 rather than the connector 402 or the connector type described in FIG. 14.

Figure 17:
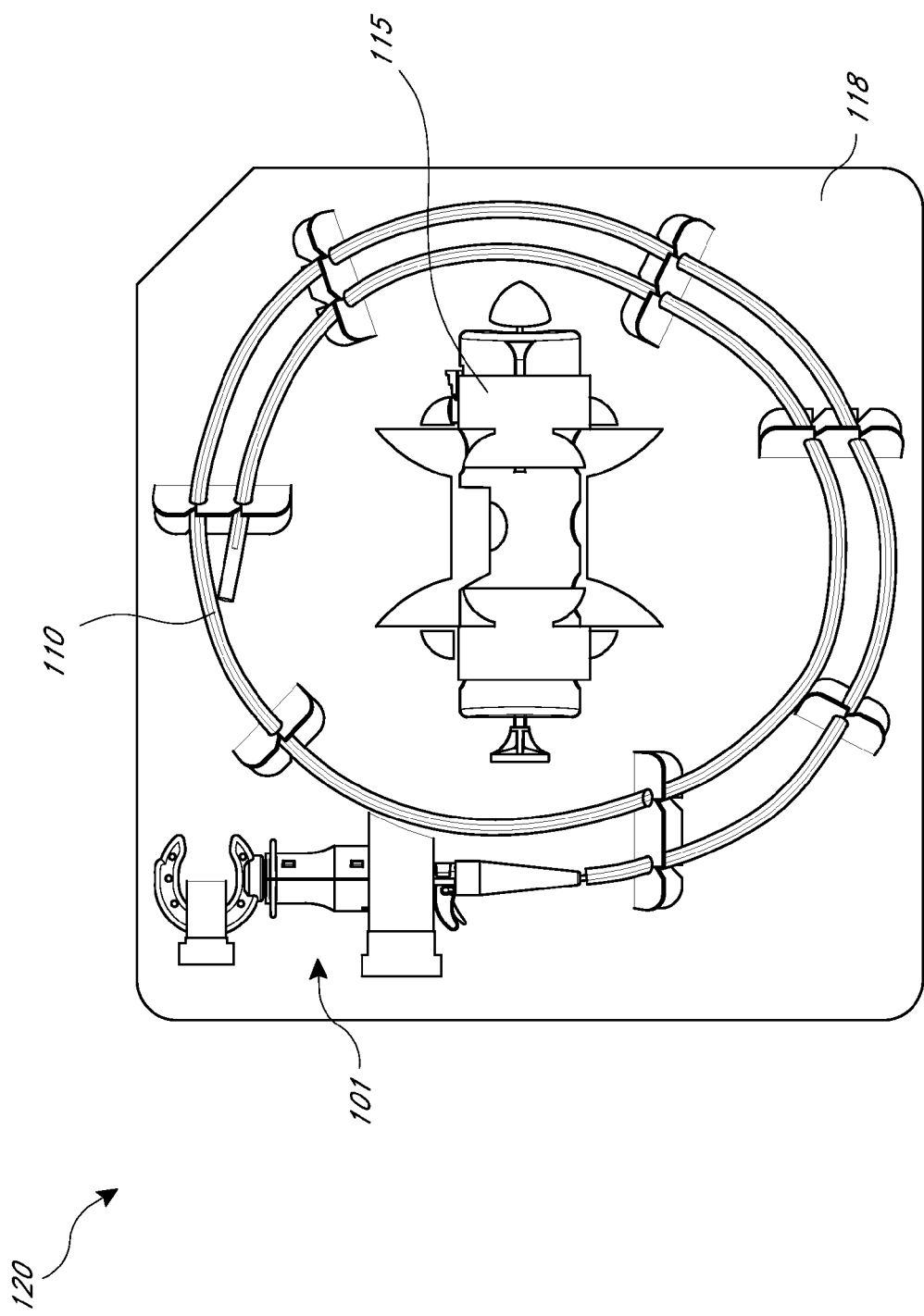
FIG. 17 is a view of an embodiment of a packaged catheter and valve loader system.

With reference now to FIG. 17, the catheter system 101 may be packaged with a tube 110 serving to protect the catheter shaft portion 105 and distal tip portion 107. A valve loader 115 may also be provided, which serves to load valves or other medical devices into the distal tip portion 107. Examples of such valve loaders 115 are described in U.S. Ser. Nos. 12/249,243 and 12/422,179, each of which is hereby incorporated in their entirety. The entire system 101 and valve loader 115 may be packaged together using the packaging 118, and together form a kit 120.

Figure 18A:
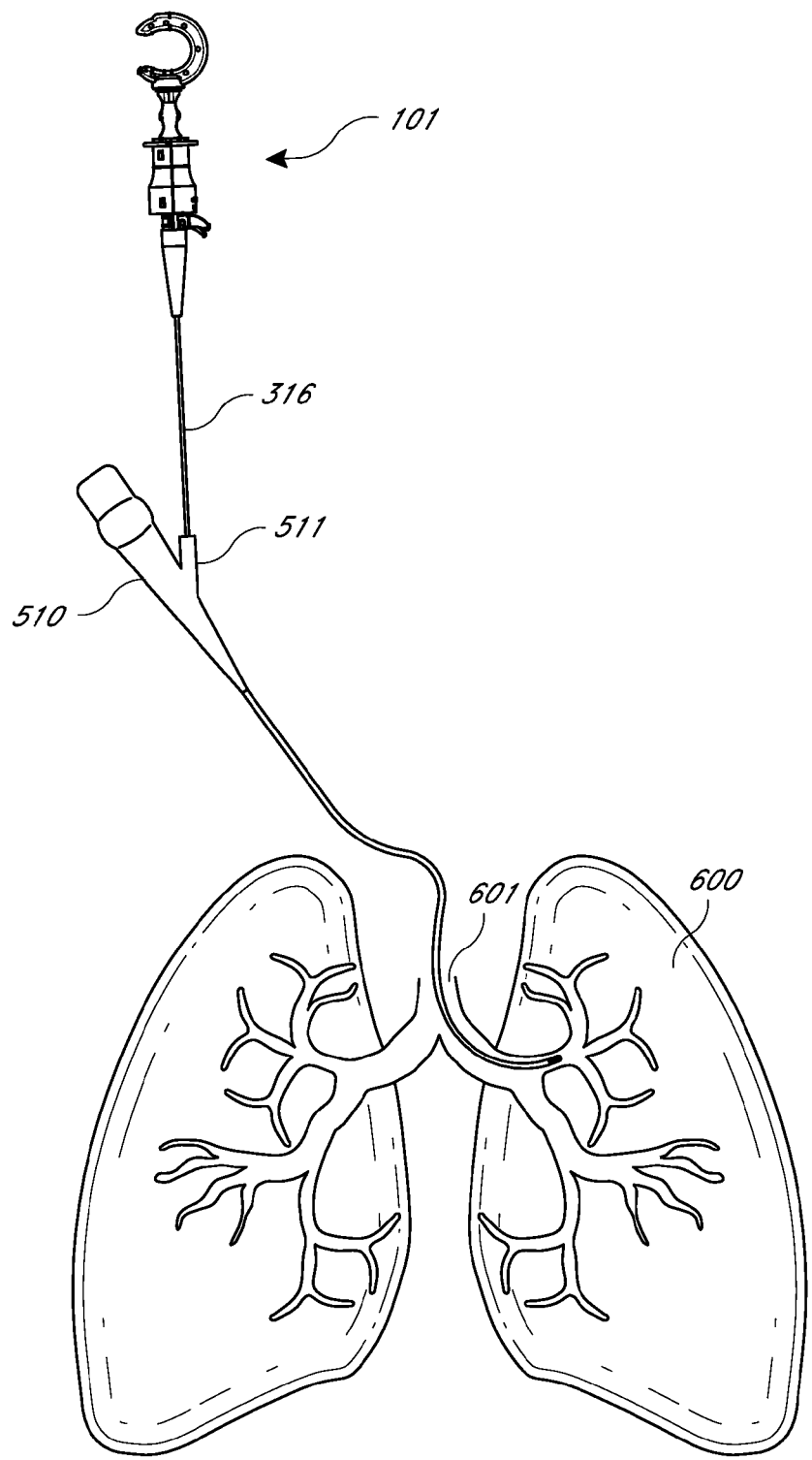
FIG. 18A illustrates an embodiment of the catheter loaded into a bronchoscope inserted into a lung airway.

FIG. 18A illustrates a possible use of the catheter system 101. Here, the catheter system 101 may be inserted into a working channel 511 of a bronchoscope 510. The bronchoscope 510 may be a commercially available model, such as the BF-P180 made by Olympus. Preferably, such a bronchoscope will be provided with at least a 2.0 mm working channel, in addition to a visualization channel permitting navigation of the bronchoscope into a patient airway 601 leading into lungs 600. Of course, endoscopes other than bronchoscopes may be used for different procedures, and such endoscopes will preferably be provided with at least a 2.0 mm working channel. Endoscopes (including bronchoscopes) used with the system 101 will preferably not exceed a length of 110 cm.

Figure 18B:
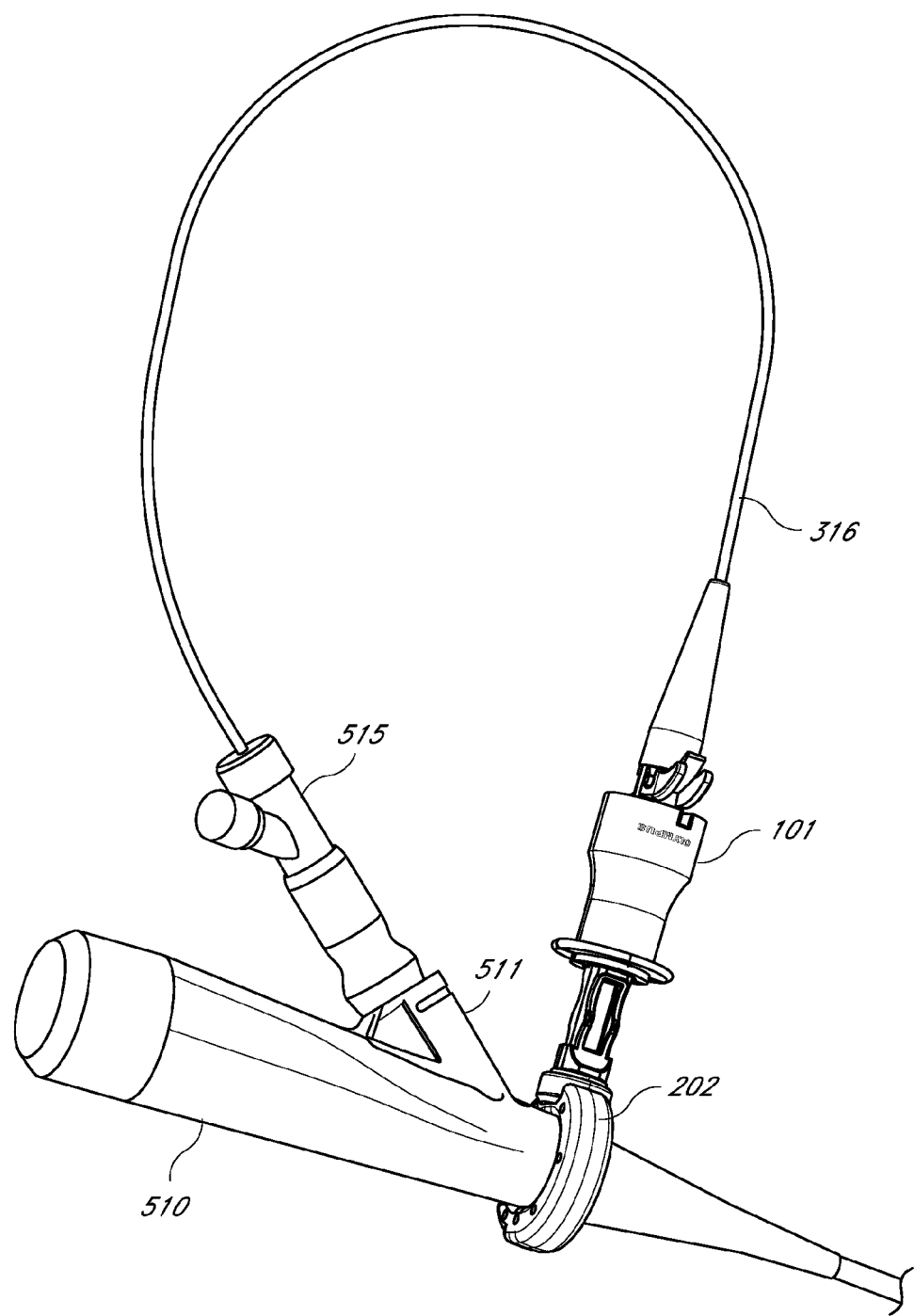
FIG. 18B illustrates an embodiment of a catheter with a grip attached to a bronchoscope.

FIG. 18B illustrates an alternative method of using the catheter system 101 with the bronchoscope 510. Here, the grip 202 can be clipped onto a part of the bronchoscope 510 as illustrated, with the bronchoscope being received within a recess in the grip 202. Some embodiments of the grip 202 may be constructed so to form a C-handle, which may advantageously permit a more secure connection to be made with the bronchoscope. After the grip 202 is secured to the bronchoscope 510, the catheter shaft portion 105 and distal tip portion 107 are inserted into the working channel 511 of the bronchoscope 510. In some embodiments, it may be advantageous to use a Tuohy-Borst adapter 515 as presently illustrated. As the Tuohy-Borst adapter 515 aids in securing the outer catheter sheath 316, accuracy in placement of the device may not require a second person or other securement method to pinch or hold the catheter sheath during deployment.

Figure 19A:
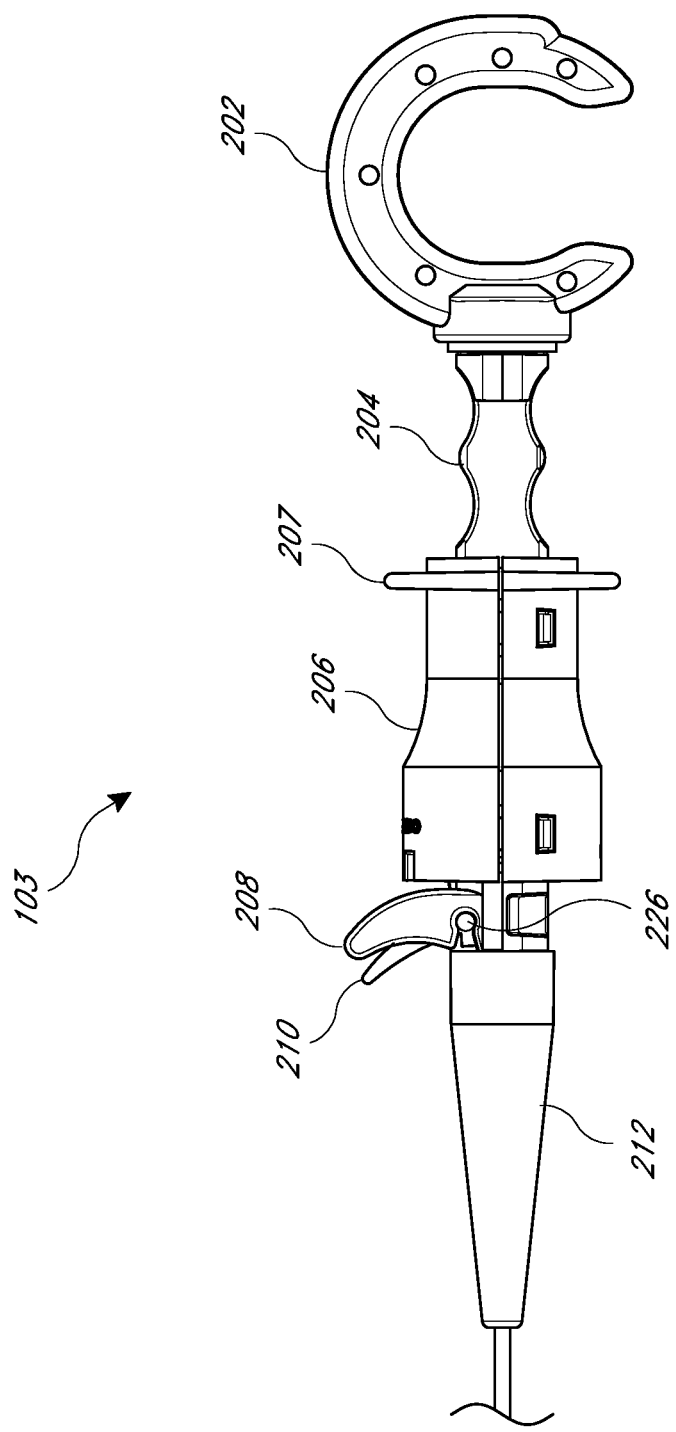
FIGS. 19A-C illustrate how a lockout mechanism present in an embodiment of the catheter handle operates.
Figure 19B:
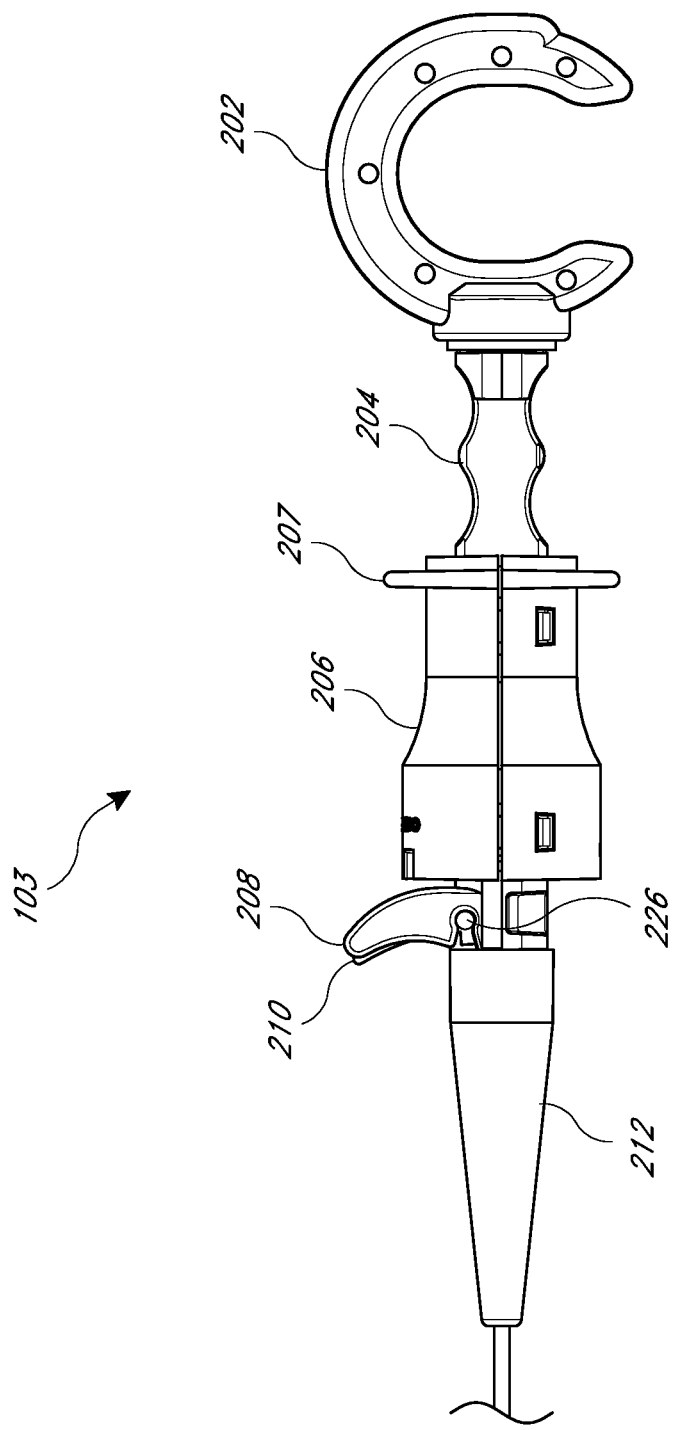
Figure 19C:
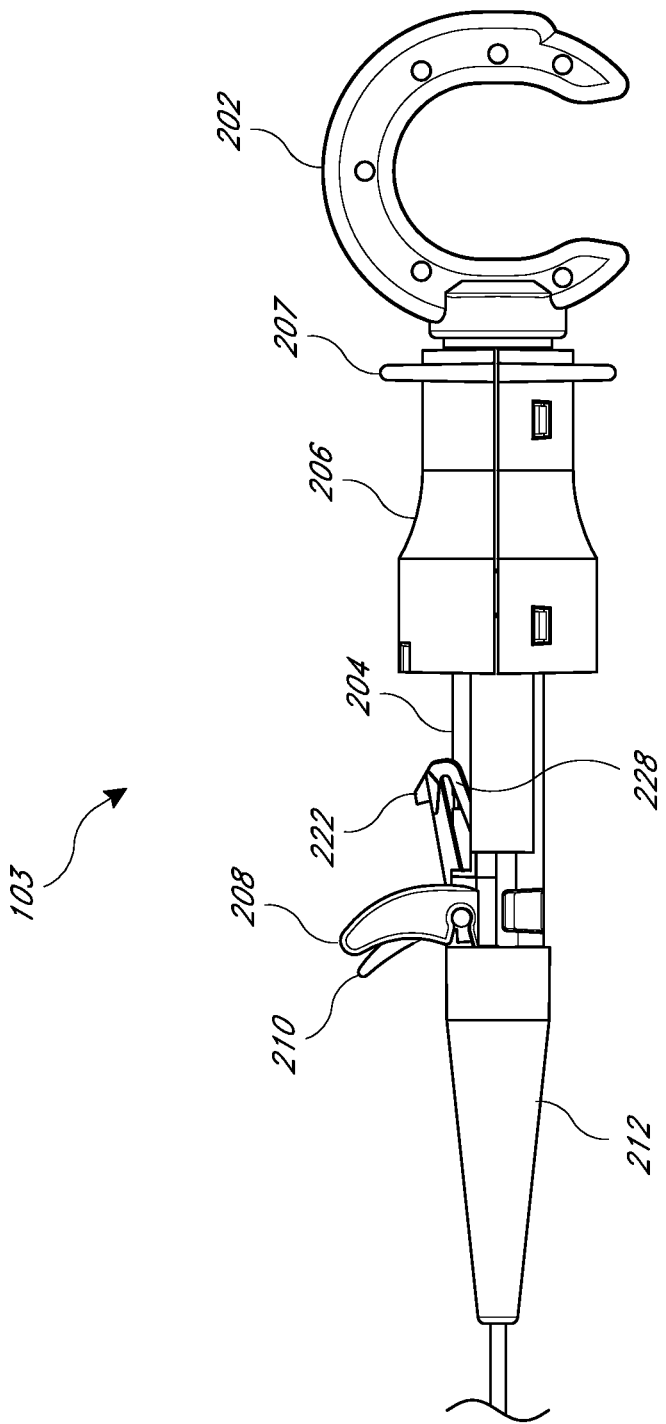

FIGS. 19A-C illustrate the use and disengagement of an embodiment of a lockout mechanism that may be used in certain embodiments described herewith. FIG. 19A represents an initial configuration of the handle portion 103 that the system 101 preferably is provided with subsequent to loading a valve or other medical device therein. Here, the locking lever 210 is in the locked position, which in this embodiment occurs when the locking lever 210 extends distally in relation to the securement tab 208. As illustrated in FIG. 8 and described above, when the locking lever 210 is in this position, the locking tab 222 attached to the locking lever 210 is engaged with the recess 220 on the movable handle 206, thus reducing or eliminating the likelihood of the movable handle 206 moving.

FIG. 19B illustrates the system 101 in an unlocked (but undeployed) position. Here, the locking lever 210 has been pushed toward the securement tab 208, in this case by pivoting the locking lever 210 about the pivot point 226. When in this position, and again with reference to FIG. 8, the locking tab 222 pivots or moves downward and becomes disengaged from the recess 220 on the movable handle 206, thus permitting the movable handle 206 to be slid axially in a proximal longitudinal direction toward the grip 202.

FIG. 19C illustrates the configuration of the handle portion 103 after the deployment of a device loaded in the distal tip 107. Here, the movable handle 206 has been slid or moved axially in a proximal longitudinal direction toward the grip 202. Some embodiments may provide for the locking lever 210 to automatically reset to a locked position. For example, after the movable handle 206 moves past the end of the locking tab 222, a spring or other restoring force may push or pivot the locking lever 210 back toward a locked position, for example via a spring 228 attached under the locking tab 222 (as illustrated in FIG. 8). Accordingly, should a user slide the movable handle 206 back in a distal direction, the handle portion 203 will have been automatically reset to the configuration illustrated in FIG. 19A, thus permitting deployment of another device without necessitating the user to remember to reset the lockout lever 210.

Figure 20A:
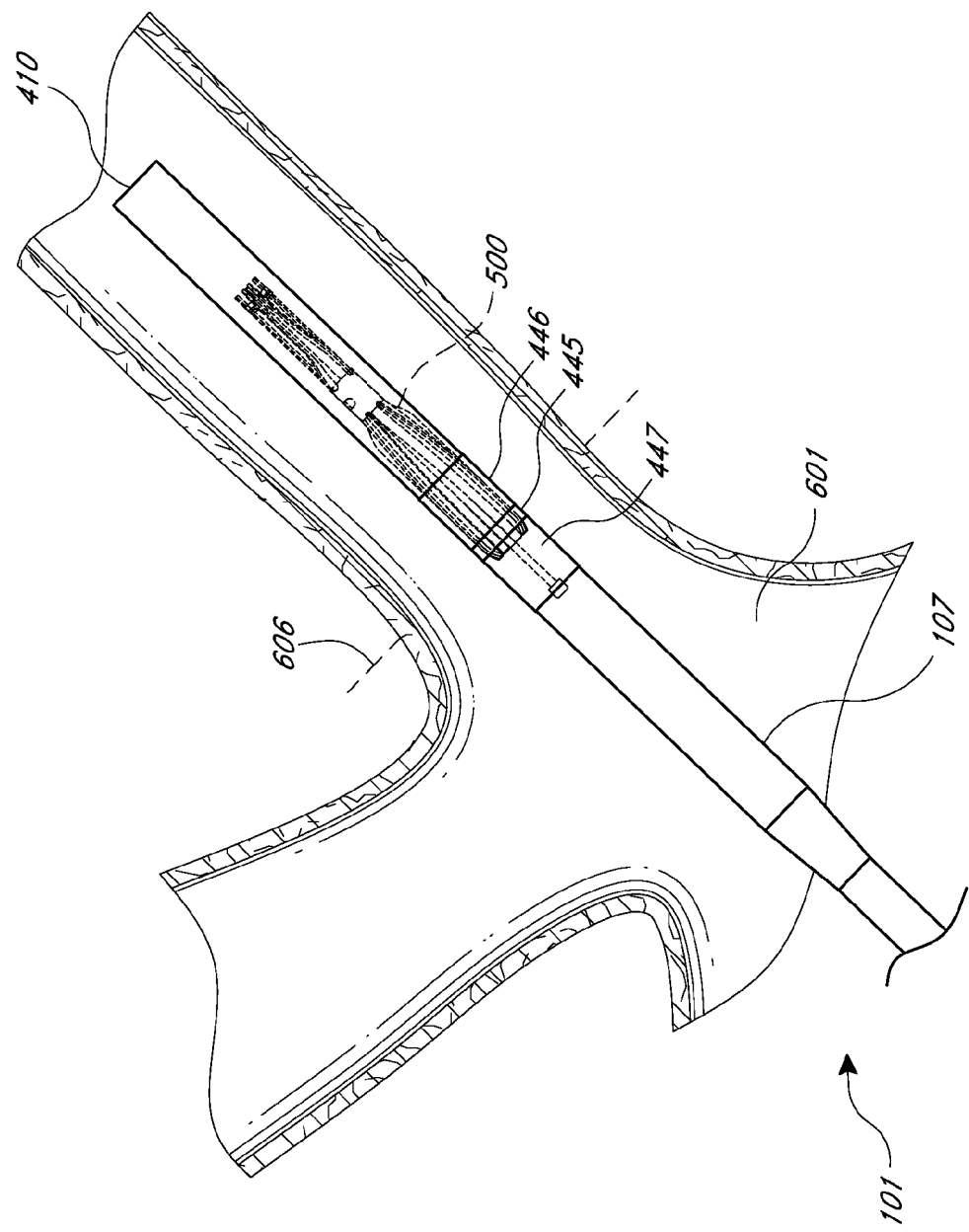
FIGS. 20A-C illustrate the deployment of a valve into an airway using a valve loaded into an embodiment of the catheter.
Figure 20B:
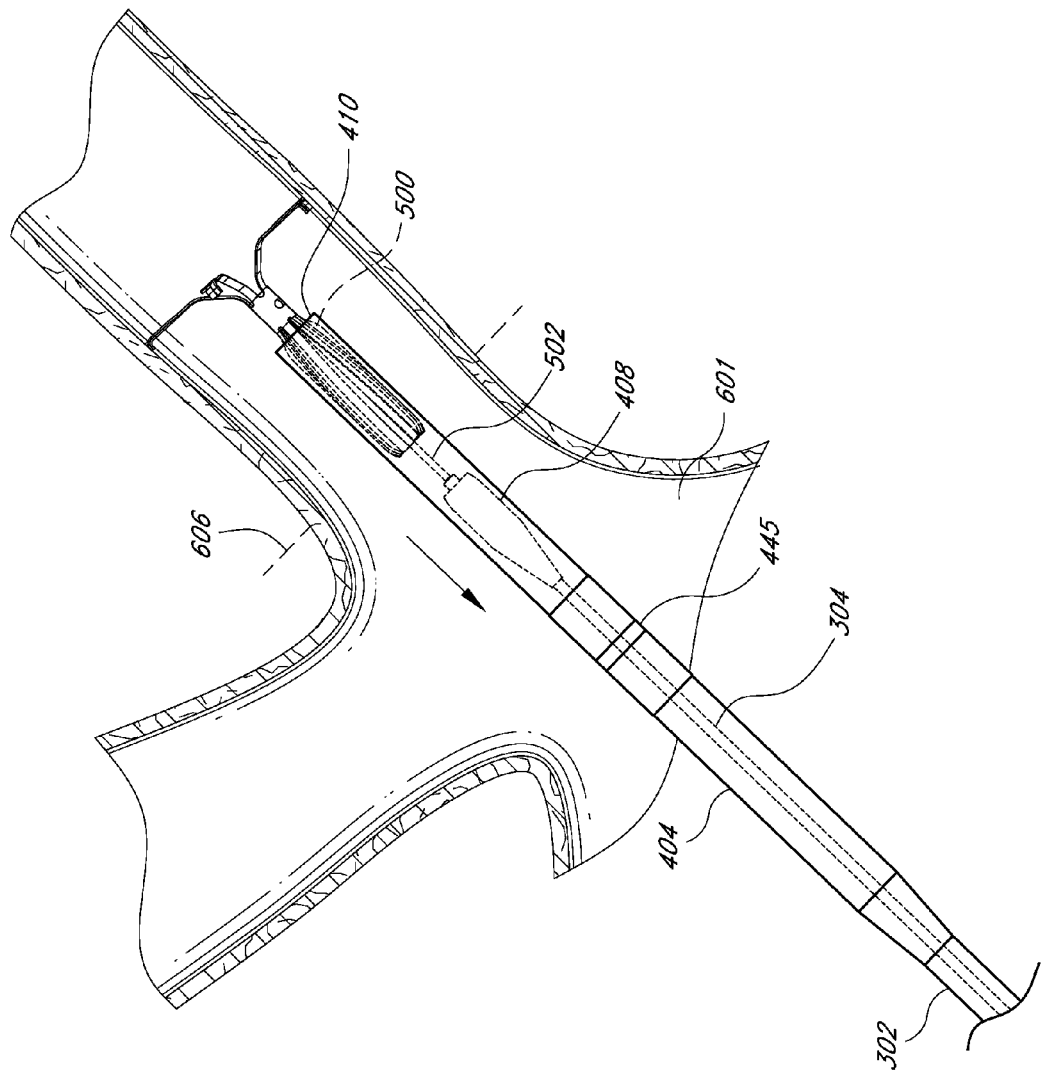
Figure 20C:
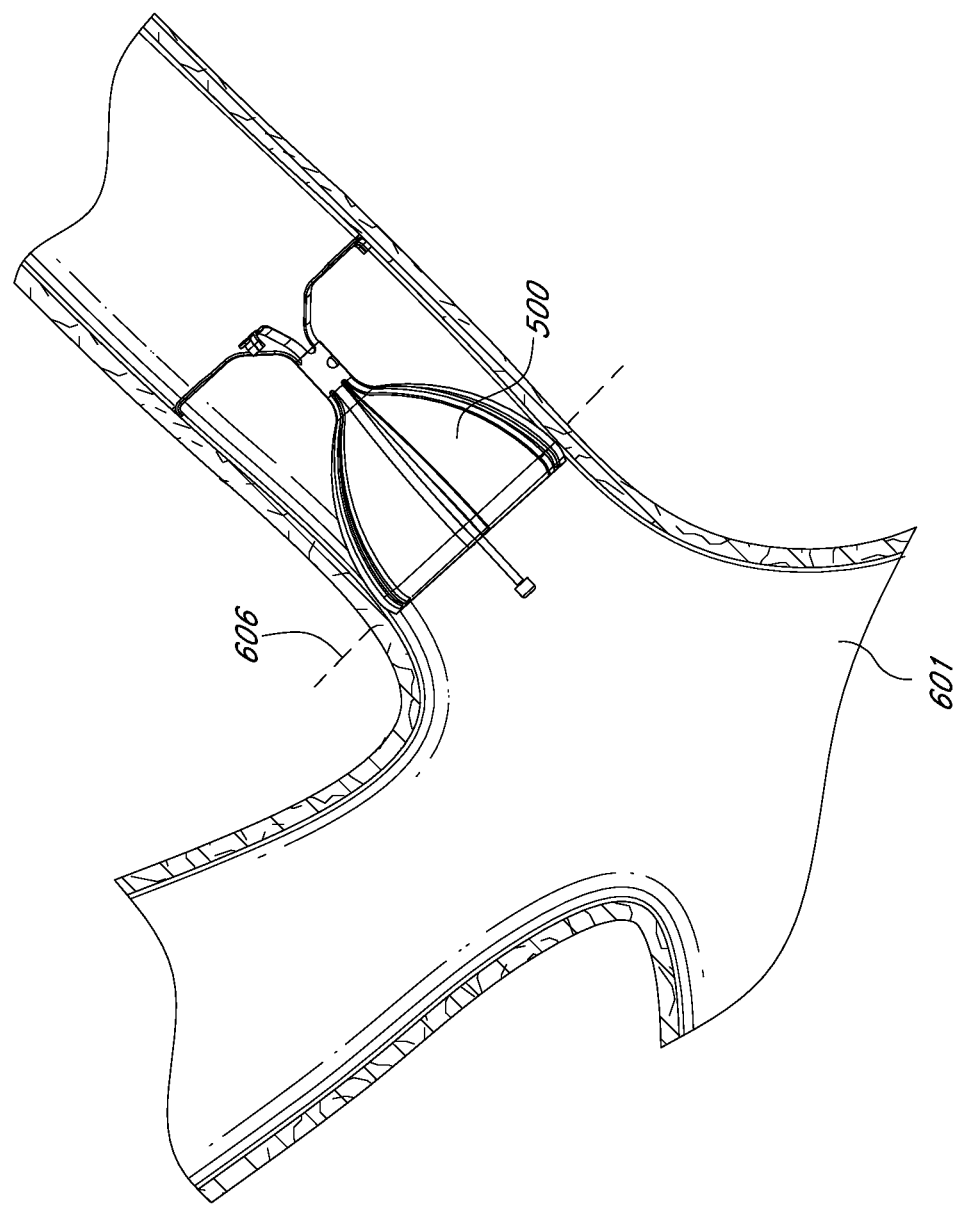

FIGS. 20A-C show an embodiment of catheter system 101 with a valve 500 loaded within a cavity 405 in the distal tip portion 107. Note that several structural elements have been depicted in ghosted lines or are not illustrated for the sake of clarity. The catheter system 101 has been inserted into a bronchoscope (not shown), and the bronchoscope is guided to a portion of a lung requiring treatment, which in this case is an airway 601.

In determining an appropriate deployment site for the valve 500 (here, denoted as deployment site 606), an operator may use the line 445 to align the distal tip portion 107 with the site 606 where the valve will be deployed, as the valve 500 will be released from the distal end 410 of the catheter at the approximate location denoted by the line 445. In some embodiments, the line 445 generally aligns with an air passageway region that the valve 500 will seal against, and can thus be aligned with a desired deployment site 606. The lines 446, 447 that flank the line 445 are preferably darker- or black-colored so as to provide additional contrast to allow an operator to easily see the line 445 through a bronchoscope viewing port. Moreover, in use an operator can extend the catheter distally beyond the line 447 and then retract the catheter proximally until reaching the line 445. While retracting the first line 447 encountered can be used as a landmark indicating that the line 445 is approaching. If so provided, a long localization marker 448 present on the distal portion of the catheter shaft portion 105 (as described in FIG. 15) may also be advantageous as another safety feature to ensure that the operator does not extend the catheter too far past the bronchoscope.

With the line 445 aligned with the desired deployment site 606, and with the locking lever 210 moved to its unlocked position, the operator pulls the movable handle 206 in a proximal direction toward the grip 202 (see generally FIGS. 19A-C). This deployment movement retracts the catheter shaft 302 and cage 404, while the stabilization wire 304 remains generally stationary. The pusher plunger 408 at the end of the stabilization wire 304 preferably is configured to contact a central rod 502 of a valve 500 inserted into the cavity 405, thereby maintaining the valve 500 in substantially the same position while the cage 404 is retracted around it. Freed from the catheter through the distal opening 410, the anchors of the valve 500 expand to make contact with the air passageway 601's wall, and the valve 500 expands so that the apex of its cup portion makes contact generally at the site 606 selected along the lung airway 601. This deployment method is useful as it permits a device to be deployed very close to the selected deployment site 606 by alignment with the line 445. Because the distal tip portion 107 retracts around the device (such as the valve 500), such a device can be positioned and deployed more accurately than other prior art devices which simply eject a device from the distal end of a catheter.

Some embodiments of the catheter system 101 may also conform to certain benchmarks and specifications in order to function acceptably in certain situations and applications. For example, in an embodiment of the system 101 being used to deploy a valve in an airway, and as described above, the system 101 will be partially inserted into the working channel 511 of a bronchoscope 510. Because the bronchoscope 510 will be inserted and navigated through tortuous airways of a patient, the system 101 within it must be able to flex sufficiently and withstand the forces that will be applied to it, which include torsional, bending, and kinking forces. Preferably, the system 101, and in particular the catheter shaft portion 105, is configured to balance the need to be sufficiently rigid so as to transmit forces used to navigate the system 101 to a suitable deployment site while being flexible enough to navigate through tortuous spaces and reduce the likelihood of injuring or perforating an airway wall if extended past the bronchoscope working channel. Further, the system 101 preferably is designed so that a possible failure of any component will not leave parts within a patient.

As the system 101 will typically encounter tensional or pulling forces during operation, the distal tip portion 107 preferably is configured to remain attached to the catheter shaft portion 105 to reduce or eliminate the likelihood of leaving portions behind in a patient. The distal tip portion 107 is also preferably resistant to kinking of the cage 404 or other components thereof, as this may affect successful delivery and deployment of medical devices loaded therein.

As illustrated in FIGS. 19A-C and 20A-C, embodiments of the system 101 are preferably configured such that its components cause minimal binding and resistance to movement during insertion and manipulation in a bronchoscope as well as during deployment of a device loaded in the distal tip portion 107. The exterior of the catheter shaft portion 105 and the distal tip portion 107 are both preferably configured to be relatively smooth and cause minimal friction, such that these components may slide freely in a bronchoscope working channel. Further, the friction between the stabilization wire 304 and the interior of the catheter shaft 302 and/or distal tip portion 107 should preferably be minimized as well. Preferably, the force required to overcome the friction of a device (such as a valve 500) loaded in the cavity 405 of the distal tip 107 should be less than the force that can be applied through the handle portion 103 by deploying the system 101 as discussed in FIGS. 19A-C and 20A-C. Such embodiments, when configured in this manner, may provide for a smoother, more accurate deployment of a device to a target site.

In use, a user will insert the bronchoscope 510 into the lung of a patient to be treated with a device to be deployed from the catheter system 101. Then, the catheter system 101 (with a device such as a valve 500 having been preloaded into the cavity 405 of distal tip 107) is inserted into the working channel 511 of the bronchoscope 510. After selecting and navigating to a suitable deployment site, and with reference now to FIGS. 19A-C, the locking lever 210 is moved to its unlocked position.

After verifying the position of the distal tip portion 107 in relation to the deployment site, which may include aligning the desired deployment site with any localization markings such as line 445 (illustrated in FIG. 15), the user slides the sliding barrel 206 in a proximal direction toward the grip 202, thereby deploying the medical device (such as the valve 500) in the deployment site at the airway of the patient.

In some embodiments, the accuracy of the catheter device deployment may be increased by pinching or otherwise securing the outer sheath 316 on the catheter shaft portion to keep the stabilization wire 304 in a relatively stationary position while the catheter shaft 302 retracts proximally. In a preferred embodiment, the catheter 101 may be removed from the bronchoscope working channel 511, and the movable handle 206 returned to its initial position so as to be reloaded with another device. Thus, multiple device deployments may be made into a patient airway without necessarily having to remove the bronchoscope 510 from the lungs 600 of a patient.

It will be understood that the present illustration of the catheter system 101 being deployed into a lung is not limiting, and that the system 101 may be used for deployment of various devices into other locations on a patient, including gastric, endoscopic, or other suitable locations. Similarly, a bronchoscope is not necessary, and other suitable devices capable of accommodating the system 101 and being guided to a deployment location may also be used, including without limitation various endoscopes or laparoscopic cannulas.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:

1. A deployment catheter for deploying a device into a lung, the deployment catheter comprising:
   a proximal end comprising a handle portion, the handle portion comprising a plunger, the plunger being surrounded by a movable handle, the movable handle configured to be slid axially in a direction along at least a portion of the length of the plunger, and wherein the plunger further comprises a locking lever capable of switching between locked and unlocked positions, the locking lever configured to prevent the movable handle from sliding in a proximal direction toward the plunger when in the locked position, but configured to permit the movable handle to slide in a proximal direction when in the unlocked position, and wherein the locking lever is further configured to reset to a locked position;
   a catheter shaft portion, the catheter shaft portion comprising a catheter shaft and a stabilization wire inside the catheter shaft, wherein the catheter shaft is secured to the movable handle at the proximal end of the catheter shaft, and wherein the stabilization wire is secured to the plunger; and
   a distal tip portion configured to receive a medical device in a cavity, wherein the distal tip portion is secured to the distal end of the hollow catheter shaft, and which further comprises a pusher plunger received within the cavity, the pusher plunger connected to the distal end of the stabilization wire.

2. The apparatus of claim 1, wherein the proximal plunger further comprises a C-shaped handle on its proximal end.

3. The apparatus of claim 1, wherein the locking lever comprises a locking tab configured to engage with a recess in the movable handle.

4. The apparatus of claim 1, wherein the locking lever comprises a spring attached to the locking lever configured to reset the locking lever to a locked position after the medical device has been deployed from the deployment catheter.

5. The apparatus of claim 1, wherein the catheter shaft portion comprises a high flexibility region at its distal end.

6. The apparatus of claim 5, wherein the high flexibility region is in a jigsaw configuration.

7. The apparatus of claim 5, wherein the high flexibility region is in a serpentine configuration.

8. The apparatus of claim 5, wherein the high flexibility region comprises overlapping discontinuous straight cuts.

9. The apparatus of claim 1, wherein the distal tip portion comprises a cage with at least one cavity configured to receive a medical device.

10. The apparatus of claim 9, wherein the cage has an arrangement of struts forming a spiral configuration.

11. The apparatus of claim 9, wherein the cage comprises one or more large fenestrations.

12. The apparatus of claim 11, wherein the one ace or more large fenestrations are configured to permit visualization and confirmation that the medical device has been loaded into the cavity.

13. The apparatus of claim 1, wherein the distal tip portion comprises at least one localization marker configured to indicate the approximate deployment location of the medical device.

14. The apparatus of claim 13, wherein the localization marker is yellow and flanked by two additional black bands.

15. The apparatus of claim 1, wherein the distal end of the catheter shaft portion further comprises at least one long localization marker.

16. The apparatus of claim 1, wherein the handle portion further comprises a frustroconical strain relief surrounding a proximal region of the catheter shaft portion.

17. The apparatus of claim 1, further comprising an outer sheath surrounding at least a proximal region of the catheter shaft portion.

18. The apparatus of claim 1, wherein the deployment catheter is configured to be loaded within a bronchoscope.

* * * * *